US011061020B2

(12) United States Patent
de Callier et al.

(10) Patent No.: US 11,061,020 B2
(45) Date of Patent: Jul. 13, 2021

(54) INTERACTIVE TEST DEVICE AND APPARATUS WITH TIMING MECHANISM

(71) Applicant: Quidel Corporation, San Diego, CA (US)

(72) Inventors: Rhys de Callier, San Marcos, CA (US); Richard L. Egan, Oceanside, CA (US); William J. Ferenczy, La Jolla, CA (US); Michael Jon Hale, San Diego, CA (US)

(73) Assignee: Quidel Corporation, San Diego, CA (US)

( * ) Notice: Subject to any disclaimer, the term of this patent is extended or adjusted under 35 U.S.C. 154(b) by 195 days.

(21) Appl. No.: 13/783,065

(22) Filed: Mar. 1, 2013

(65) Prior Publication Data

US 2013/0230845 A1  Sep. 5, 2013

Related U.S. Application Data

(60) Provisional application No. 61/757,023, filed on Jan. 25, 2013, provisional application No. 61/666,689, filed on Jun. 29, 2012, provisional application No. 61/636,105, filed on Apr. 20, 2012, provisional application No. 61/605,694, filed on Mar. 1, 2012.

(51) Int. Cl.
*G01N 33/53* (2006.01)
*G01N 33/558* (2006.01)
*G01N 33/58* (2006.01)

(52) U.S. Cl.
CPC ....... *G01N 33/5302* (2013.01); *G01N 33/558* (2013.01); *G01N 33/585* (2013.01)

(58) Field of Classification Search
None
See application file for complete search history.

(56) References Cited

U.S. PATENT DOCUMENTS

| 4,934,817 | A | 6/1990 | Gassenhuber |
| 5,204,264 | A | 4/1993 | Kaminer et al. |
| 5,238,737 | A | 8/1993 | Burkhardt et al. |
| 5,414,258 | A | 5/1995 | Liang |
| 5,766,961 | A | 6/1998 | Pawlak |
| 5,770,460 | A | 6/1998 | Pawlak et al. |
| 6,074,616 | A | 6/2000 | Buechler et al. |
| 6,136,610 | A | 10/2000 | Polito et al. |
| 6,144,455 | A | 11/2000 | Tuunanen et al. |
| 6,267,722 | B1 | 7/2001 | Anderson et al. |
| 6,392,894 | B1 | 5/2002 | Buechler et al. |
| 6,394,952 | B1 | 5/2002 | Anderson et al. |
| 6,727,073 | B1 | 4/2004 | Moore et al. |
| 6,830,731 | B1 | 12/2004 | Buechler et al. |
| 6,867,051 | B1 | 3/2005 | Anderson et al. |
| 6,878,947 | B2 | 4/2005 | Haberstroh |
| 6,936,476 | B1 | 8/2005 | Anderson et al. |
| 7,002,688 | B2 | 2/2006 | Aravanis et al. |
| 7,437,913 | B2 | 10/2008 | Djennati et al. |
| 7,521,249 | B2 | 4/2009 | Rosen et al. |
| 7,521,260 | B2 | 4/2009 | Petruno et al. |
| D606,664 | S | 12/2009 | Jacono et al. |
| 7,632,687 | B2 | 12/2009 | Gokhan |
| 7,784,678 | B2 * | 8/2010 | Kuo ................ G01N 35/00732 235/375 |
| 7,784,679 | B2 | 8/2010 | Kuo et al. |
| 7,925,445 | B2 | 4/2011 | Petrilla et al. |
| 8,039,783 | B2 | 10/2011 | Lai |
| 8,043,667 | B1 | 10/2011 | Petruno et al. |
| 8,128,871 | B2 | 3/2012 | Petruno et al. |
| 8,334,522 | B2 | 12/2012 | Egger |
| 9,207,181 | B2 | 12/2015 | Egan et al. |
| 2002/0190356 | A1 | 12/2002 | Buechler et al. |
| 2004/0018637 | A1 | 1/2004 | Polito et al. |
| 2004/0241047 | A1 | 12/2004 | Buechler et al. |
| 2005/0008538 | A1 * | 1/2005 | Anderson ............ G01N 33/558 422/411 |
| 2005/0017076 | A1 | 1/2005 | Hosokawa et al. |

(Continued)

FOREIGN PATENT DOCUMENTS

| CN | 2653511 Y | 11/2004 |
| CN | 1766580 A | 5/2006 |

(Continued)

OTHER PUBLICATIONS

U.S. Appl. No. 13/783,019, Egan et al., filed Mar. 1, 2013.
Egan et al., "High sensitivity immunofluorescence influenza A+B assay with reader", 27th Annual Clinical Virology Symposium, May 8-11, 2011, 1 page (2011) Abstract.
Van Dyke et al., "Multiplex point of care (POC) assay for the detection community acquired resoiratory viruses", 27th Annual Clinical Virology Symposium, Poser, May 8-11, 2011, 2 pages (2011) Abstract.
International Search Report from related PCT Patent Application No. PCT/US2013/028743 dated May 28, 2013.
International Search Report from PCT Patent Application No. PCT/US2013/028749 dated Jul. 1, 2013, application now published as PCT Publication No. WO2013/131057 on Sep. 6, 2013.

(Continued)

*Primary Examiner* — Ellen J Marcsisin
(74) *Attorney, Agent, or Firm* — McDermott Will & Emery LLP; Judy M. Mohr; Brett A. Schweers

(57) ABSTRACT

A system comprised of an apparatus and a test device is described. The test device and the apparatus are designed to interact to determine the presence or absence of an analyte of interest in a sample placed on the test device. The test device and apparatus interact to provide a timer feature for determining a test device specific adjustable cut-off value that is used to ascertain whether signal from a test line in the device corresponds to a positive or negative results, irrespective of the time elapsed since placement of sample on the test device. The adjustable cut-off value renders the system relatively insensitive to incubation time of the test device, where if the incubation time is shorter or longer than needed for accuracy of a test result, the analyzer will report an invalid result, thus preventing the reporting of an incorrect (false negative or false positive) result.

8 Claims, 21 Drawing Sheets

(56) References Cited

U.S. PATENT DOCUMENTS

| | | |
|---|---|---|
| 2006/0228554 A1 | 10/2006 | Tan et al. |
| 2007/0154970 A1 | 7/2007 | Albuechler et al. |
| 2007/0236692 A1 | 10/2007 | Schebesta et al. |
| 2008/0031779 A1 | 2/2008 | Polito et al. |
| 2008/0081341 A1* | 4/2008 | Maher et al. .............. 435/7.1 |
| 2008/0199851 A1 | 8/2008 | Egan et al. |
| 2008/0311002 A1 | 12/2008 | Kirby et al. |
| 2009/0061507 A1 | 3/2009 | Ho |
| 2009/0090874 A1 | 4/2009 | Roper et al. |
| 2009/0142856 A1 | 6/2009 | Hudak et al. |
| 2009/0263854 A1 | 10/2009 | Jacono et al. |
| 2010/0068826 A1 | 3/2010 | Gokhan |
| 2010/0117003 A1 | 5/2010 | Egger |
| 2010/0135857 A1 | 6/2010 | Hunter et al. |
| 2010/0311181 A1 | 12/2010 | Abraham et al. |
| 2011/0043618 A1 | 2/2011 | Salisbury et al. |
| 2012/0021531 A1 | 1/2012 | Ellis et al. |
| 2012/0071342 A1 | 3/2012 | Lochhead et al. |
| 2012/0223251 A1 | 9/2012 | Morrow et al. |
| 2012/0300205 A1 | 11/2012 | Misener et al. |
| 2013/0230844 A1 | 9/2013 | Egan et al. |
| 2013/0230845 A1 | 9/2013 | Egan et al. |
| 2016/0054316 A1 | 2/2016 | Egan et al. |

FOREIGN PATENT DOCUMENTS

| | | |
|---|---|---|
| EP | 0174722 A2 | 3/1986 |
| JP | 2003-083970 A | 3/2003 |
| WO | WO 1999/039298 A1 | 8/1999 |
| WO | WO 2000/031539 A1 | 6/2000 |
| WO | WO 2005/031355 A1 | 4/2005 |
| WO | WO 2009/014787 A2 | 1/2009 |
| WO | WO 2010/081219 A1 | 7/2010 |
| WO | WO 2013/131052 A1 | 9/2013 |
| WO | WO 2013/131057 A1 | 9/2013 |

OTHER PUBLICATIONS

Giebeler et al., "Performance validation for microplate fluorimeters", vol. 15, No. 3, p. 363-375 (2005).

International Search Report from PCT Patent Application No. PCT/US2014/068829 dated Mar. 6, 2015.

Ahn et al., "Development of a point-of-care assay system for high-sensitivity C-reactive protein in whole blood", Clinica Chimica Acta, vol. 332. pp. 51-59 (2003).

* cited by examiner

INTERACTIVE TEST DEVICE AND APPARATUS WITH TIMING MECHANISM

CROSS-REFERENCE TO RELATED APPLICATIONS

This application claims the benefit of U.S. Provisional Application No. 61/605,694, filed Mar. 1, 2012, and of U.S. Provisional Application No. 61/636,105, filed Apr. 20, 2012, and of U.S. Provisional Application No. 61/666,689, filed Jun. 29, 2012, and of U.S. Provisional Application No. 61/757,023, filed Jan. 25, 2013. Each of the aforementioned priority documents is incorporated herein by reference in its entirety.

TECHNICAL FIELD

The subject matter described herein relates to a system and an apparatus for analysis of a sample to aid in medical diagnosis or detection of the presence or absence of an analyte in the sample.

BACKGROUND

Assay devices for detection of an analyte in a sample are long known in the art and include detection gels, microfluidic devices, immunoassays, and the like. In particular, lateral flow immunoassay devices are routinely used for detecting the presence of an analyte in a sample. Lateral flow immunoassay devices utilized a labeled specific binding reagent that is releasably immobilised on a test strip of porous material. A liquid sample, such as a biological sample from a human or an environmental sample, is applied to one end of the porous strip and the capillary properties of the strip transports the liquid sample along the strip, releasing the labeled specific binding reagent, which binds specifically to the analyte of interest at a first binding site thereof, if present, in the sample. The labeled binding reagent is then typically captured at a test zone by a second reagent having specific binding for a second binding site of the analyte of interest. Excess labeled binding reagent is captured at a control zone, downstream of the test zone by a control reagent which binds specifically to the labeled reagent.

Such lateral flow assay devices are commercially available, for example, to detect pregnancy by the presence of a human chorionic gonadotropin (hCG) in a urine sample applied to the test device. In such tests, two signals visible by the naked eye of the user are generated. One signal is a 'control' signal, and is formed by the localization of derivatized blue latex beads. The latex beads are coated with an immunoglobulin molecule and are captured by a capture antibody, deposited in a line on the test strip generally perpendicular to the direction of sample flow, the capture antibody having specific binding activity for the immunoglobulin carried on the beads. The generation of this signal informs the user that (i) neither the immunoglobulin on the latex bead, nor the capture antibody on the test stick, have been sufficiently denatured or otherwise degraded during manufacture or storage of the test kit significantly to interfere with the specific binding between the two molecules; and (ii) sufficient liquid sample has been applied to mobilize the releasably immobilized latex beads and to transport them along the test stick at least as far as the "control" zone, in which the capture antibody is located. A urine sample containing hCG contacted with the test stick in a correctly-performed assay, will cause the deposition of latex beads in both the control zone and in the test zone, resulting in the formation of two blue lines visible to the user, one line in the control zone and one line in the test zone.

It is common in most test devices, like lateral flow assay devices, to instruct the user to wait a period of time prior to reading the test result. For example, instructions in the package for the pregnancy test described above instruct the user to read the assay result one minute after removing the test stick from contact with the sample. This is because the label on the test strip is generally one readily visible to the naked eye, and a minimum amount of label must accumulate at the test and control lines before it is visible to the naked eye.

In contrast to test devices that are read with the naked eye needing to incubate for a minimum period of time prior to reading the result, devices that are read by an apparatus, i.e., assays that are not visually read with the naked eye, under incubation is generally not a concern because of the superior sensitivity, relative to the eye, and ability to detect wavelengths not visible to the naked eye of an optical system in an apparatus.

One approach to solving the problem of under incubation in test devices, such as lateral flow assay devices, read by the naked eye is to incorporate a timer signal or line into the assay device. For example, the test strip can include components that interact, after a pre-determined time interval after application of the sample to the test device, to create a detectable color change. These additional 'timer' reagents are deposited in a 'timer' section of the test strip and, upon hydration by the sample, interact to produce a color change. In another approach, the control line in the assay device is modified to delay appearance of its signal until a desired incubation time has elapsed, so that the control line becomes a dual purpose line of signaling the device operated correctly and for signaling that sufficient time has elapsed to read the test line. Delaying the appearance of the signal from the control line can be done by moving the control line further downstream in the device or by material changes at the control line that obscure the line for a period of time.

These approaches, however, are not needed, and therefore not suitable, for a test device, like a lateral flow assay device, that is read by an instrument or apparatus. Test devices to be instrument read have an entirely different concern in terms of timing for read than do devices read with the naked human eye. One concern is that because of the superior sensitivity of the instrument in detecting signal from the control and test lines that the device will be read after too much incubation time has elapsed. That is, if the sample is applied and the device incubates for too long, the signal may be above the cut-off value set in the instrument to report a result, leading to no result being ascertainable, an invalid result, or an incorrect result (false negative or false positive). The present invention provides a solution to this problem.

BRIEF SUMMARY

The following aspects and embodiments thereof described and illustrated below are meant to be exemplary and illustrative, not limiting in scope.

In one aspect, an apparatus for detection of a signal from a test device indicative of the presence or absence of an analyte in a sample is provided.

In another aspect, a system comprised of a test device and an instrument or apparatus (also referred to as an analyzer) are provided. The test device comprises a first population of detectable particles for detection of an analyte in a sample and a second population of detectable particles for specific binding to a non-test analyte. The analyzer is capable of receiving the test device (also referred to as a "test strip"), where the analyzer comprises an optical system for detection of a signal generated from each of the first and second populations of particles when each population reaches a specific position on the test strip. The signal detected from all or a portion of the second population of particles is used to determine a cut-off value for the analyzer to determine whether signal from all or a portion of the first population of particles indicates presence of analyte in the sample and to render analyzer detection of signal from all or a portion of the first population of particles insensitive to incubation time over a time period of 3-10 minutes. Alternatively, a ratio of signal detected from all or a portion of the second population of particles to signal detected from all or a portion of the first population of particles determines a cut-off value for the analyzer to determine presence or absence of analyte in the sample.

In one embodiment, the test device is a lateral flow immunoassay test device.

In one embodiment, the second population of detectable particles have specific binding to a specific non-test analyte. In another embodiment, the first population of detectable particles have specific binding to a specific test analyte.

In yet another embodiment, the signal from all or a portion of the first population of particles is manipulated or transformed by an algorithm in the analyzer to provide a quantitative or semi-quantitative amount of analyte present in the sample.

In one embodiment, signal from the second population of detectable particles is mathematically transformed by an algorithm in the analyzer to provide a transformed signal.

In yet another embodiment, the signal from the second population of detectable particles is mathematically transformed using an exponential transformation. In various embodiments, the exponential transformation comprises raising the signal from all or a portion of the second population of detectable particles by an exponent selected from 1.2, 1.3, 1.4, 1.5, 1.6, 1.7 and 1.8. In another embodiment, the mathematical transformation is a logarithmic transformation of the signal from all or a portion of the second population of detectable particles.

In one embodiment, the exponentially transformed signal is multiplied by a constant value specific for an analyte to yield a transformed cut-off value, individually determined for the test strip. In one embodiment, the constant value is determined for each specific manufacturing lot of test strips for a particular analyte.

In one embodiment, one or both of the first and second population of detectable particles is comprised of particles comprised of a fluorescing lanthanide compound.

In an exemplary embodiment, the fluorescing lanthanide compound is europium. In another embodiment, the particles are comprised of a europium core with a polystyrene exterior.

In yet another aspect, a method for determining presence or absence of an analyte in a sample is provided. The method comprises depositing a sample on a test strip comprising a first population of detectable particles for detection of an analyte in a sample and a second population of detectable particles for specific binding to a non-test analyte. The test strip (or test device) is inserted into an analyzer capable of receiving the test strip, the analyzer comprising an optical system for detection of a signal generated from each of the first and second populations of particles when each population reaches a specific position on the test strip. An intensity of signal from all or a portion of the second population of particles is detected, and a cut-off value is calculated by an algorithm in the software of the analyzer to determine whether the signal from all or a portion of the first population of particles corresponds to the presence or absence of analyte in the sample. A result is then reported by the analyzer.

In one embodiment, the analyte of interest is a protein. In an exemplary embodiment, the protein in human chorionic gonadotropin.

In another embodiment, the analyte of interest is an infectious analyte. In an exemplary embodiment, the infectious analyte is a virus or a bacteria. In still another embodiment, the infectious analyte is influenza A or influenza B.

Additional embodiments of the present systems, apparatus and methods will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the system, apparatus or method. Additional aspects and advantages of the present systems and apparatus are set forth in the following description and claims, particularly when considered in conjunction with the accompanying examples and drawings.

DETAILED DESCRIPTION

I. Definitions

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

As used in this specification, the singular forms "a," "an," and "the" include plural referents unless the context clearly dictates otherwise. Thus, for example, reference to an "antibody" includes a single antibody as well as two or more of the same or different antibodies, reference to an "excipient" includes a single excipient as well as two or more of the same or different excipients, and the like.

II. System

In one aspect, a system comprised of a test device and an apparatus capable of optically detecting a signal are provided. The test device and the apparatus are designed for unique interaction with each other, as will now be described.

In the description below, the test device is exemplified by a lateral flow immunoassay test strip, and is sometimes referred to as a test strip. It will be appreciated that the test device is not intended to be limited to the lateral flow immunoassay test device used to exemplify the system, and a skilled artisan will appreciate that other test devices, such as microfluidic devices, immunoassays other than lateral flow based immunoassays, are contemplated.

Test Device: Exemplary Lateral Flow Immunoassay

Figure 1:
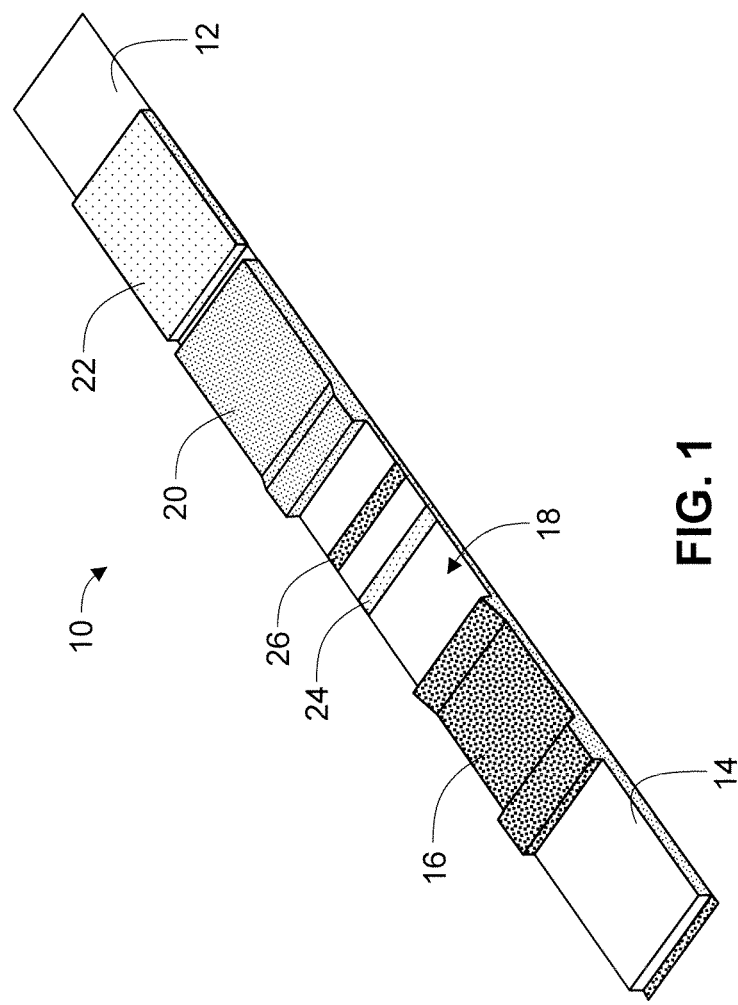
FIG. 1 is a perspective view of one embodiment of a test device, exemplified by a lateral flow immunoassay.

FIG. 1 is a perspective view of a test device, exemplified in this embodiment by a lateral flow immunoassay test strip 10. In the embodiment shown, test strip 10 is not situated within an external housing member, although it will be appreciated that the test strip can be contained within a housing, rigid or flexible, for improved handling by a user. Test strip 10 is comprised of a porous support member 12, that may extend the length of the test strip. The support member is generally made from any of a variety of materials through which the sample is capable of passing. For example, the material may be, but is not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; and the like.

Test strip 10 also comprises, in a downstream to upstream direction, a sample pad 14, a label pad 16, a detection zone 18, an absorbent pad 20, and an optional desiccant 22. Detection zone 18 is comprised of a test line 24 and a reference line 26. The sample pad 14 is in fluid communication with the label pad which is in fluid communication with the support member in the detection zone on which the test line and reference line are deposited. Some suitable materials that may be used to form the sample pad include, but are not limited to, nitrocellulose, cellulose, porous polyethylene pads, and glass fiber filter paper. If desired, the sample pad may also contain one or more assay pretreatment reagents, either diffusively or non-diffusively attached thereto. The label pad 16 is formed from a material through which the sample is capable of passing. For example, in one embodiment, the label pad is formed from glass fibers. Although only one label pad is shown, it should be understood that multiple label pads may be present.

Deposited on the label pad are a first population of a labeled reagent with specific binding to the analyte of interest, and a second population of a labeled reagent with specific binding to an analyte that is not the analyte of interest; i.e., specific binding to an analyte other than the analyte of interest or, alternatively, specific binding to a specific analyte other than the analyte of interest. In one embodiment, the labeled reagent in the first and second populations comprise a collection of beads or particles (also referred to a microparticles) derivatized on their external surfaces with a respective specific binding member. For example, in one embodiment, the first population is a population of detectable particles capable of specific binding to an analyte of interest. The second population is a population of detectable particles capable of specific binding to an analyte other than the analyte of interest, and in one embodiment, capable of specific binding to a specific analyte other than the analyte of interest (also referred to as a non-test analyte).

The detectable substance to which the specific binding members are associated (ionically or covalently) may be a luminescent compound that produces an optically detectable signal. For example, suitable fluorescent molecules may include, but are not limited to, fluorescein, europium chelates, phycobiliprotein, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth.

The detectable reagent, in one embodiment, is a compound that has a relatively long emission lifetime, and has a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In some embodiments, the luminescent compounds have a Stokes shift of greater than about 50 nanometers, in some embodiments greater than about 100 nanometers, and in some embodiments, from about 100 to about 350 nanometers. Exemplary fluorescent compounds having a large Stokes shift include lanthanide chelates of samarium (Sm (III)), dysprosium (Dy (III)), europium (Eu (III)), and terbium (Tb (III)). These chelates may exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent labels. These chelates additionally have a narrow emission spectra, typically having bandwidths less than about 10 nanometers at about 50% emission. One suitable europium chelate is N-(p-isothiocyanatobenzyl)-diethylene triamine tetraacetic acid-$Eu^3$.

The detectable substance may take the form of a particle or bead, and in particular a synthetic particle or bead. In one embodiment, latex particles that are labeled with a fluorescent or colored dye are utilized. In another embodiment, a particle with a fluorescent, phosphorescent or luminescent core coated with a polymer is utilized, the polymer surrounding the core typically formed from polystyrene, butadiene styrenes, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth.

The specific binding members attached to the particles may be antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte (i.e., "analog") may be used so long as it has at least one epitope in common with the analyte.

The specific binding members may generally be attached to the detectable particles using any of a variety of well-known techniques. For instance, covalent attachment of the specific binding members to the detectable particles may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the detectable particles may contain a relatively high surface concentration of polar groups. In addition, although detectable particles are often functionalized after synthesis, such as with poly(thiophenol), the detectable particles may be capable of direct covalent linking with a protein without the need for further modification.

In one embodiment, the label pad of the immunoassay test strip comprises a first population of mobilizable detectable particles that bind specifically to an analyte of interest in a sample. The label pad also includes a second population of mobilizable detectable particles that bind specifically to an analyte other than the analyte of interest in a sample, In one example, the first population of particles comprise a monoclonal antibody for specific binding with a protein analyte of interest, such a human chorionic gonadotropin (hCG), and the second population of particles comprise an antibody with specific binding to immunoglobulin G. For example, each particle in the second population of particles is derivatized with an antibody with specific binding to the alpha chain of hCG. Each particle in the second population of particles is derivatized to comprise a goat anti-rabbit IgG antibody, for specific binding to IgG protein in the sample.

With continuing reference to FIG. 1, test line 24 comprises a binding member that is immobilized on the support membrane 12. The immobilized binding member in the test line serves to capture particles in the first population of particles that comprise a binding member specific for the analyte of interest, and in this way captures on the test line all or a portion of the detectable particles in the first population that have bound to the analyte of interest. The immobilized binding member preferably binds specifically to the analyte of interest at a location different from the binding site for the detectable particle and the analyte of interest. The immobilized binding member at the test line can be any of the binding members listed above, including an antibody, an antigen, and the like.

The detection zone in the test strip also comprises a reference line 26. Reference line 26 comprises a binding member that is immobilized on the support membrane 12. The immobilized binding member in the reference line serves to capture particles in the second population of particles that comprise a binding member specific for an analyte other than the analyte of interest, and in this way captures on the reference line all or a portion of the detectable particles in the second population. The immobilized binding member preferably binds specifically to a non-test analyte at a location different from the binding site for the detectable particle and non-test analyte. The immobilized binding member at the reference line can be any of the binding members listed above, including an antibody, an antigen, and the like.

Figure 2:
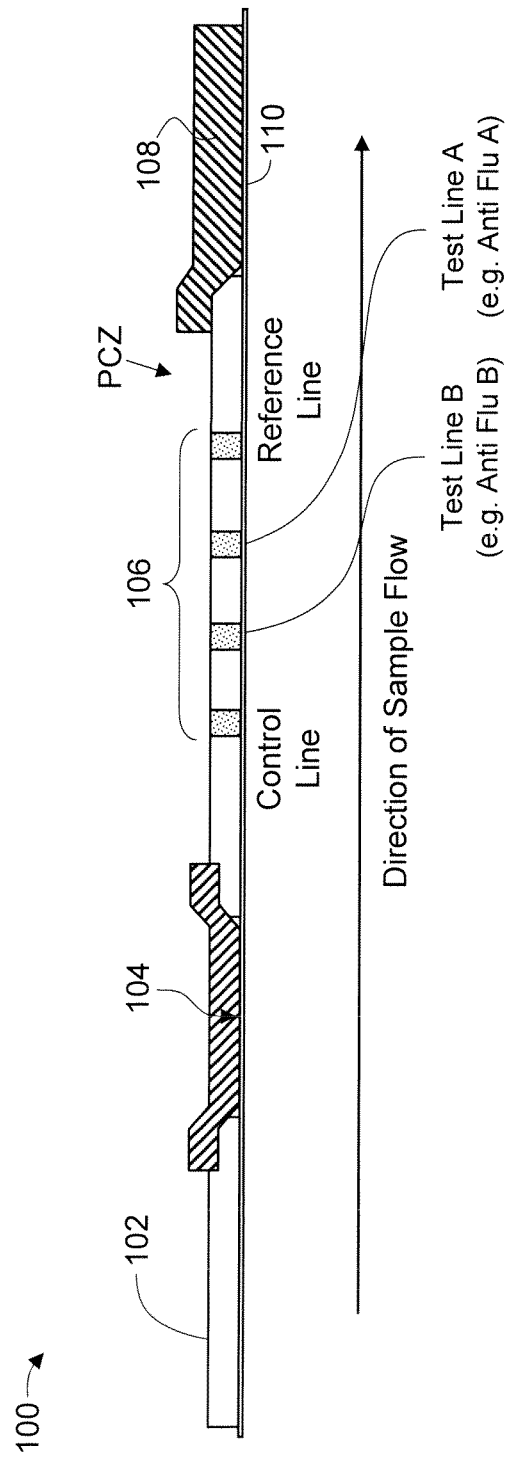
FIG. 2 is a perspective view of another embodiment of a test device, exemplified by a lateral flow immunoassay test strip.
Figure 3A:
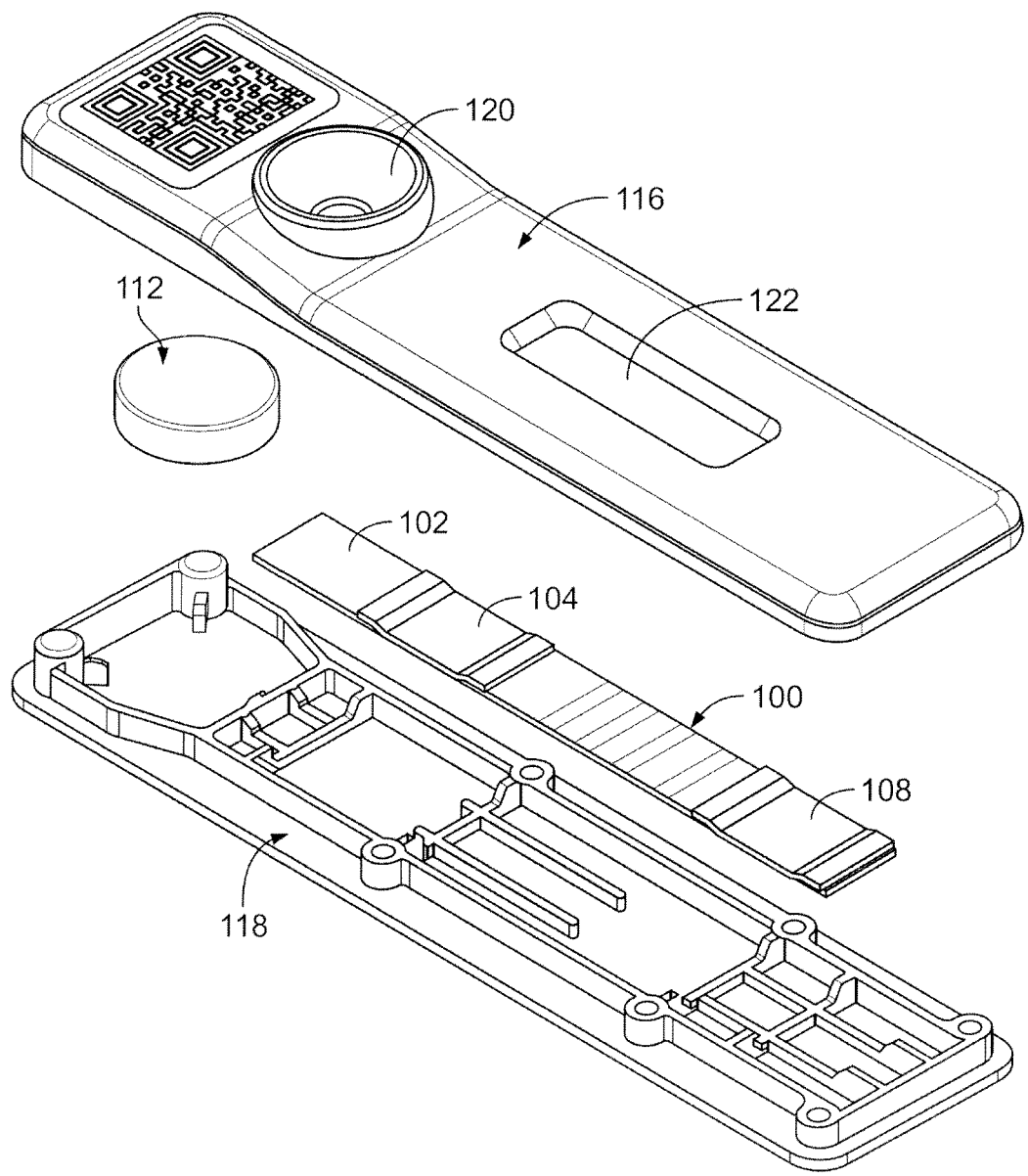
FIGS. 3A-3B are illustrations of a test strips enclosed in a housing sized for insertion into a drawer of an apparatus.
Figure 3B:
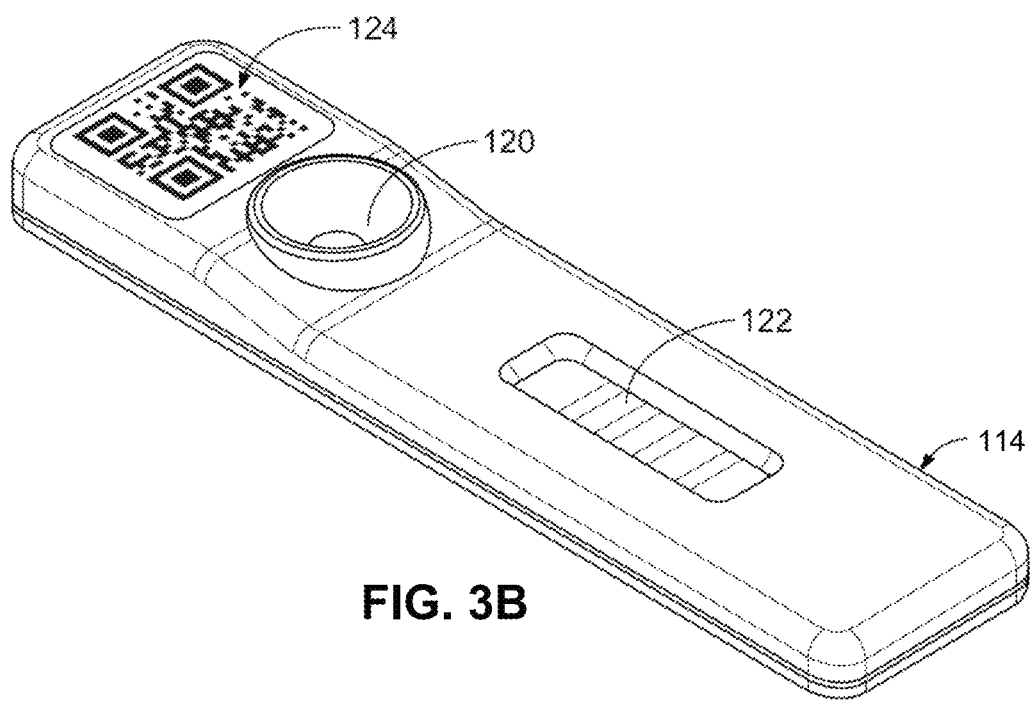

Another embodiment of an test device is shown in FIG. 2 and FIGS. 3A-3B. The test device is in the form of a test strip 100 is comprised of, in sequence, a sample pad 102, a label pad 104, one or more lines indicated collectively at 106 and selected from a test line, a control line and a reference line, and an absorbent pad 108. In one embodiment, a support member 110 is provided, and each or some of the sample pad, label pad, lines and absorbent pad are disposed on the support member. As will be described below with reference to FIG. 4, the test strip comprises a region between the downstream edge of the most downstream analyte-specific test line, which in the embodiment shown in FIG. 2 is test line for binding to an influenza antigen (e.g., a test line that comprises anti-flu A antibodies), and the upstream edge of the absorbent pad 108 is a procedural control zone, denoted PCZ in FIG. 2. In some embodiments, the test strip additionally includes a desiccant portion, not shown in FIG. 2, but visible in an embodiment shown FIG. 3A. A desiccant portion can be positioned on the support member of the test strip, and in one embodiment is disposed on the support member downstream of the absorbent pad, as described in U.S. Patent Application Publication No. 2008/0311002, incorporated by reference herein. In another embodiment, see in FIG. 3A, a desiccant portion 112 is a discrete component, physically separate from the test strip, inserted into a housing member that contains the test strip.

In one embodiment, the test strip is enclosed in a housing, sometimes referred to as a cassette, such as housing 114 in FIG. 3B. Together a test strip inserted into a housing form a test device. Housing 114 in this embodiment is comprised of an upper member 116 and a lower member 118 that fit together to form a housing. Lower member 118 may include architectural features that define dimensioned regions for receiving the test strip 110 and the optional desiccant 112. Upper housing member 116 includes at least two openings, a first sample input port 120 and a viewing window 122. The sample input port is disposed directly above the sample pad on the test strip, so that a sample dispensed into the sample input port contact the sample pad for flow along the test strip. In the embodiment shown, the sample input port includes a bowl portion to receive a liquid sample into the port. The viewing window is positioned to reveal the lines in the test strip, so the optics system in the apparatus can interact with the lines, as will be described below.

In the embodiment shown in FIG. 3B, a bar code label 124 is affixed to the upper housing member. It will be appreciated that the bar code label can be positioned elsewhere on the housing, and is positioned for interaction with the internal bar code scanner positioned within the apparatus. In one embodiment, the bar code label is a 2D bar code, encoding information, for example, regarding the assay test strip, such as the pathogen/analyte the test strip is designed to detect (Flu A/B, Strep A, RSV, hCG, others listed below, etc.) which that informs the apparatus what protocol in memory to initiate for scanning the test strip; a unique test serial number so that the apparatus will not read same test strip twice. In one embodiment, the information contained in the bar code does not include information related to the patient or the sample type, and is limited to information about the test strip.

It will be appreciated that the test devices illustrated in FIGS. 1-3 are exemplary of lateral flow test devices in general. The test strip can be configured uniquely for any given analyte, and the external housing is optional, and if present, need not be a cassette housing but can be a flexible laminate, such as that disclosed in U.S. Patent Application Publication No. 2009/02263854 and shown in Design U.S. Pat. No. D606664, which are both incorporated by reference herein. The system requires only that the drawer in the apparatus and the test device be dimensioned to receive the test device in the drawer, and the optics system in the apparatus have a movement path the scans the necessary regions of the test device.

Figure 4:
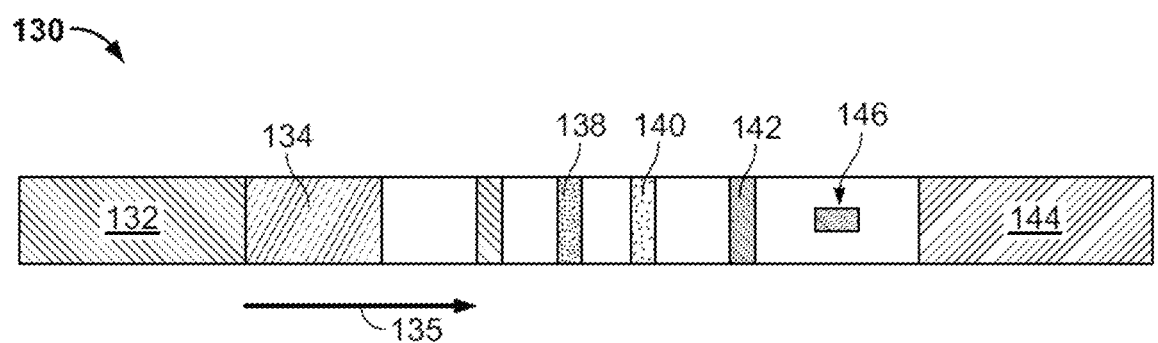
FIG. 4 is a top view of an exemplary test strip and the arrangement of its structural and immunochemical features for interaction with the apparatus.

In that regard, FIG. 4 is a top view of an exemplary test strip and the arrangement of its structural and immunochemical features for interaction with the apparatus. Test strip 130 includes a sample receiving zone 132 in fluid communication with a label zone 134. A fluid sample placed on or in the sample zone flows by capillary action from the sample zone in a downstream direction, indicated by arrow 135. Label zone 134 is in fluid communication with at least a test line and a control line or a reference line. In the embodiment shown in FIG. 4, the label zone is in fluid communication with an analyte test line 138, an optional second analyte test line 140, and a reference line 142. The two or more lines are in fluid communication with an absorbent zone 144. That is, the label zone is downstream from the sample zone, and the series of test line(s) and reference line are downstream from the label zone, and the absorbent pad is downstream from the portion of the test strip on which the lines are positioned. A region between the downstream edge of the most downstream analyte-specific test line, which in the embodiment shown in FIG. 4 is test line 140, and the upstream edge of the absorbent pad is a procedural control zone 146. Reference line 142 is within the procedural control zone 146. As will be described below, the procedural control zone, and in particular the reference line therein, (i) ascertains whether sample flow along the test strip occurred based on its RLU signal (emission), and (ii) may be used by the analyzer (or more properly, an algorithm stored within the analyzer) to determine the relative locations of the other lines (control, if present, and analyte-specific test line(s)) on the test strip. The reference line is also used to ascertain a cut-off value, as will be described below, to render the immunoassay insensitive to incubation time, and in particular insensitive to incubation time over a period of 1-15 minutes, preferably 1-12 minutes, more preferably 1-10 or 2-10 minutes.

The sample zone receives the sample suspected of containing an analyte of interest control its flow into the label zone. The label zone, in one embodiment, contains two dried conjugates that are comprised of particles containing a lanthanide element. The lanthanide materials include the fifteen elements lanthanum, cerium, praseodymium, neodymium, promethium, samarium, europium, gadolinium, terbium, dysprosium, holmium, erbium, ytterbium, lutetium, and yttrium. In one embodiment, the dried conjugates are particles which are polystyrene particles or microparticles (particles less than about 1,000 micrometers in diameter, preferably less than about 500 micrometers in diameter, more preferably less than 200, 150 or 100 micrometers in diameter) containing a luminescent or fluorescent lanthanide, wherein in one embodiment, the lanthanide is europium. In a preferred embodiment, the lanthanide is a chelated europium. The microparticles, in one embodiment, have a core of a lanthanide material with a polymeric coating, such as a europium core with polystyrene coating. A binding partner for the analyte(s) of interest in the sample is/are attached to or associated with the outer surface of the microparticles, as was described above with regard to FIG. 1. Upon entering the label zone, the liquid sample hydrates, suspends and mobilizes the dried microparticle-antibody conjugates and carries the conjugates together with the sample downstream on the test strip to the control or reference and test lines disposed on the nitrocellulose strip. If an analyte of interest is present in the sample, it will bind to its respective conjugate as the specimen and microparticles flow from the label zone onto the surface of the nitrocellulose. In the embodiment shown in FIG. 4, this flowing mixture will then a test line, such as test line 138. If the analyte of interest is present in the sample, the fluorescent microparticle-antibody conjugate which is now bound with analyte of interest, will bind to the specific binding member for the analyte of interest that is immobilized at the test line. In some embodiments, a single test line is present on the test strip. In other embodiments, at least two, or two or more test lines are present on the strip. By way of example, a test strip intended for detection and/or discrimination of influenza A and influenza B will include a first test line to detect influenza A and a second test line to detect influenza B. Microparticle-antibody conjugates comprised of microparticles coated with antibodies specific for influenza A and microparticles coated with antibodies specific for influenza B are included in the label zone. A first test line for influenza A and a second test line for influenza B are disposed downstream of the label zone. The first test line for influenza A comprises a monoclonal or polyclonal antibody to a determinant on the nucleoprotein of influenza A and the second test line for influenza B comprises a monoclonal or polyclonal antibody to a determinant on the nucleoprotein of influenza B. If antigen is present in the sample, a typical immunoassay sandwich will form on the respective test line that matches the antigen in the sample.

The microparticle-antibody conjugates that do not bind to a test line continue to flow by capillary action downstream, across the reference line and into the absorbent pad.

Liquid sample placed on the sample pad, and pulled by capillary action in the label pad, also hydrates, suspends and mobilizes the dried microparticle-antibody conjugates that have specific binding affinity for an analyte other than the analyte of interest (the test analyte). These particle-antibody conjugates interact specifically with an analyte in the sample other than the analyte of interest to form a particle-antibody-non-test analyte complex that flows down the test strip. This complex is captured at the reference line by binding interaction between a specific binding member immobilized at the reference line with affinity for the non-test analyte. In one embodiment, deposited on the reference line is a goat anti-rabbit immunoglobulin, and the particles for capture at the reference line comprise an antibody specific for the goat anti-rabbit immunoglobulin. This antibody has specific interaction with IgG immunoglobulin in the sample deposited on the strip.

Signal generated at the reference line provides information, for example, about the flow of the sample, and also can serve as a location marker to direct the apparatus to the precise other locations on the nitrocellulose that are to be scanned by the optics system, as will be described below.

The signal generated at the reference line also provides a cut-off value, that is used by the apparatus to ascertain whether signal from the test line indicates presence of the analyte of interest. This feature of the reference line will be described below, with particular regard to Example 1. First, however, the apparatus will be described.

Apparatus

Figure 5A:
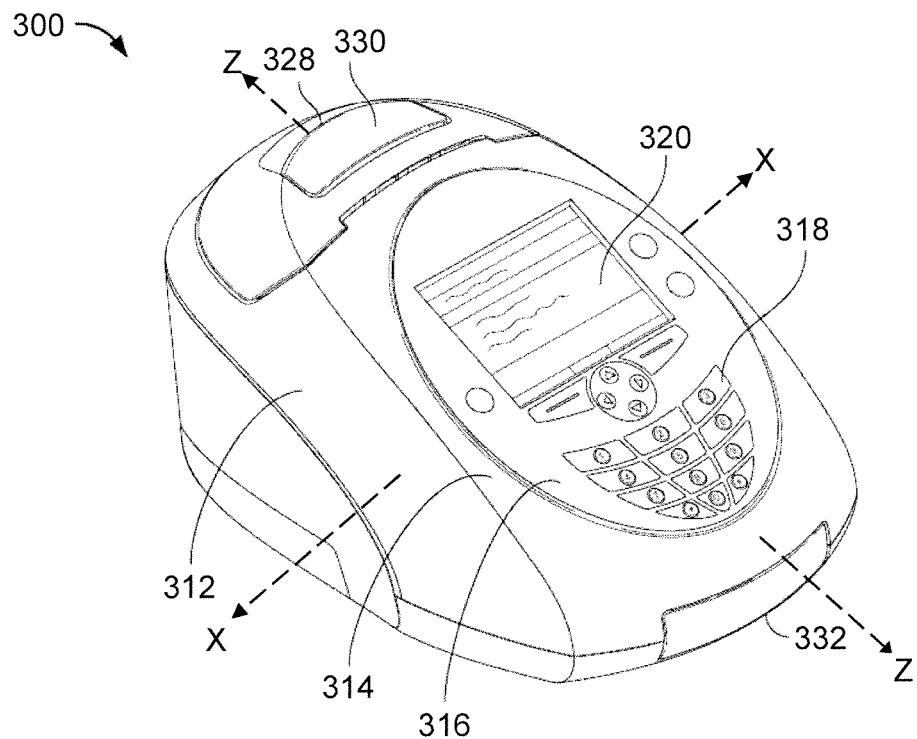
FIGS. 5A-5B are front perspective (FIG. 5A) and a back view (FIG. 5B) of an exemplary apparatus.
Figure 5B:
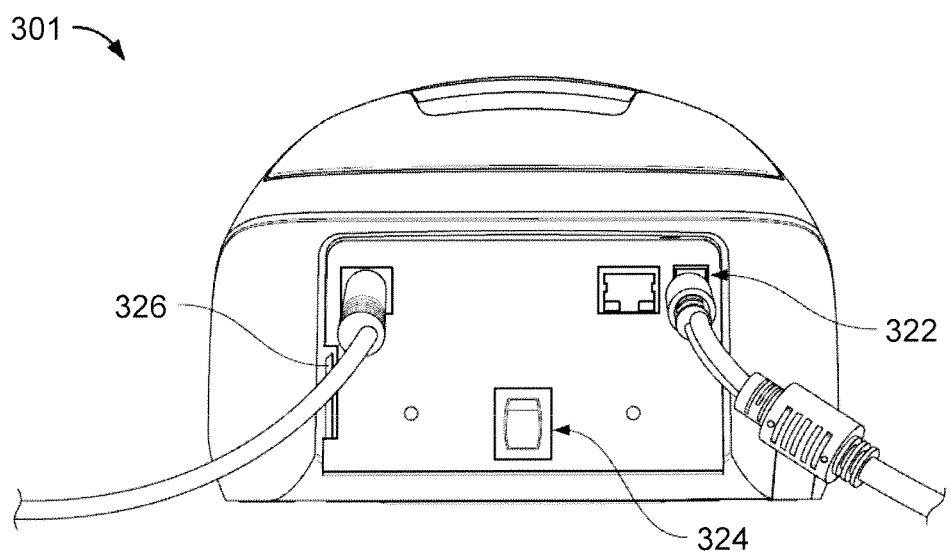

An embodiment of an apparatus capable of detecting a signal produced by a test device is illustrated in FIGS. 5A-5B. Apparatus 300 includes a housing 312 that encloses an optics system, electronics software, and other components of the apparatus, all to be described herein below. A front side 314 of the apparatus includes a user interface 316 that may include, for example, a key pad 318 and a display screen 320. The key pad includes numeric keys for entry of numeric values, which can also be labeled with letters of the alphabet, a decimal point key, a back space key, and other keys that are desired by end users. As part of the key pad or as separate keys positioned elsewhere on the apparatus, the device may include keys to print test results, to advance printer paper, to open or close a drawer in the device, directional arrow keys and soft or select keys for a user to interact and instruct the apparatus. In one embodiment, the key pad is an alpha/numeric key pad, and the apparatus includes a print key to activate print feature of a test result; a paper advance key; navigation screen keys for a user to navigate through menu options displayed on interface screen (for example, right/left/up/down keys, select keys).

The display screen can be, for example, a liquid crystal display screen, to receive output from a data processing unit in the apparatus and display it to a user of the apparatus. In one embodiment, the display screen is a touch screen, for interaction with a user. An exemplary screen is a color screen with resolution of 320×240 (¼ VGA) and adjustable contrast and brightness. Visible on the screen to a user will be information such as test results, error messages, instructions, calibration information, troubleshooting information, user information, and the like.

An embodiment of the rear panel of apparatus 300 is shown in FIG. 5B and can include port to receive a source of AC power 322 and an on/off toggle switch 324, which in this embodiment is a soft key to activate the software. The apparatus may additionally provide ports, on the rear panel or elsewhere on the apparatus, to connect optional components and/or to interface with external instruments. For example, the apparatus may include a PS2 connector, for example, to interface with an external barcode reader; a port, such as an RJ45 port, to connect to a local area network or Ethernet; a removable memory card port or slot; and/or a USB port. In a preferred embodiment, the apparatus includes a slot or port 326 for insertion of a removable non-volatile flash memory card, such as an SD card, and the apparatus is capable of read and write operations to and from the SD card, to, for example, store all scan data from each test strip, update system software.

With reference again to FIG. 5A, the apparatus can also include a printer, such as a thermal printer, resident within the housing, and an opening 328 in a removable cover 330 on the housing is provided through which paper from the internal printer exits the housing. The removable cover provides access to access or replenish a paper supply (not visible in FIG. 5A) that interacts with the printer inside the apparatus.

Figure 6A:
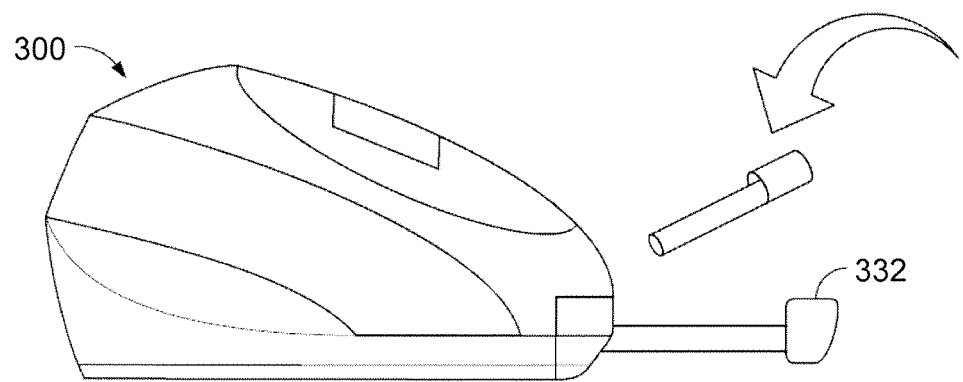
FIGS. 6A-6B are views of an exemplary apparatus showing a side view of the apparatus with the drawer in an open position (FIG. 6A) and a top perspective view of the drawer in an open position with a lateral flow immunoassay test device inserted into the drawer (FIG. 6B)
Figure 6B:
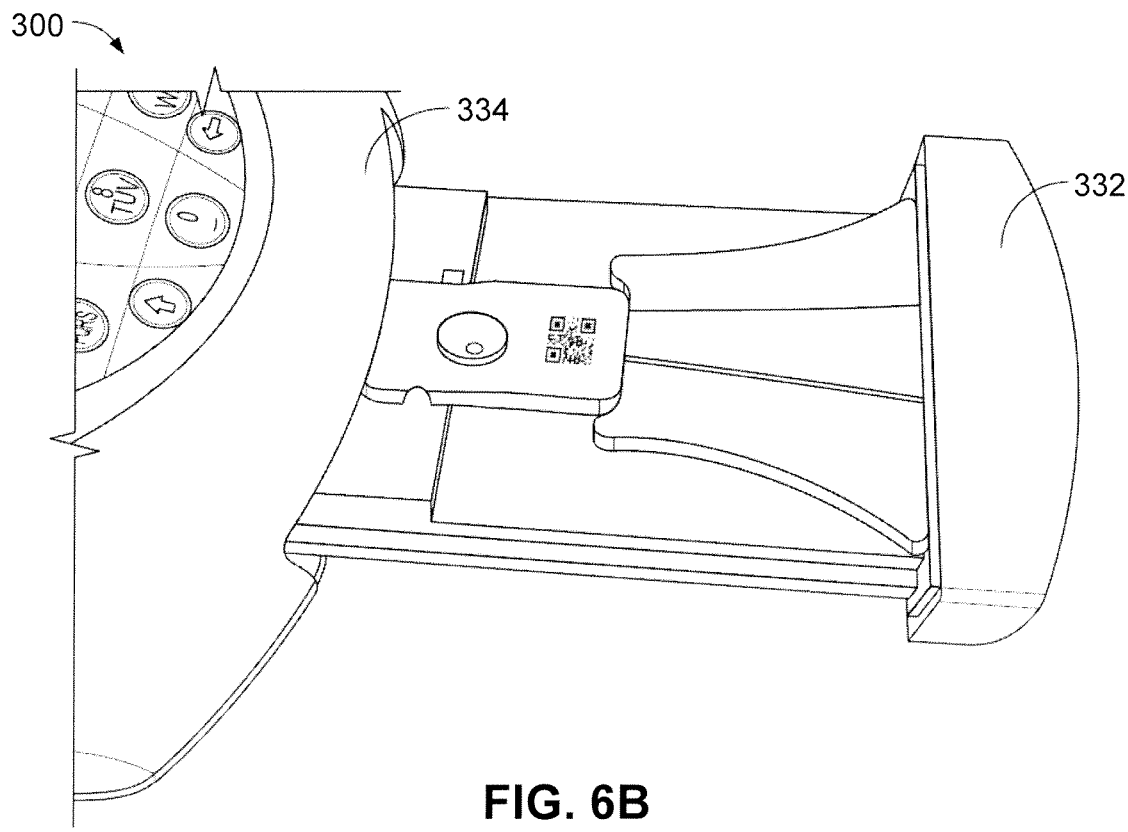

The apparatus also includes a drawer 332 movable between open and closed positions, as shown in FIG. 5A in its closed position and in FIGS. 6A-6B in its open position. In the embodiment shown, the drawer is positioned on a front edge 334 of the apparatus, as seen best in FIG. 6B. It will be appreciated that the drawer could also be positioned on either side of the apparatus. In one embodiment, the drawer moves between its open and closed positions by a mechanical mechanism, such as a latch and spring mechanism. In one embodiment, the draw opens in response to a user activating a key on the front or face of the apparatus, such as an "open drawer" or "eject test device" button. In one embodiment, the drawer is moved into its closed position after insertion of a test device manually by a user, or in response to a user activating a key or button on the apparatus. The drawer is configured to receive an immunoassay test device, further described below. Within the drawer, in one embodiment, is a distinct region, for example a depression, sized to receive the test device. During operation of the apparatus, the test device remains in a stationary position in the drawer, and therefore is positioned with precision in the apparatus for precise interaction with a movable optics system, described below. Accordingly, the drawer comprises in one embodiment a mechanism for positioning the test device for interaction with the optics system. An exemplary embodiment of a positioning mechanism is illustrated in FIGS. 7A-7B.

Figure 7A:
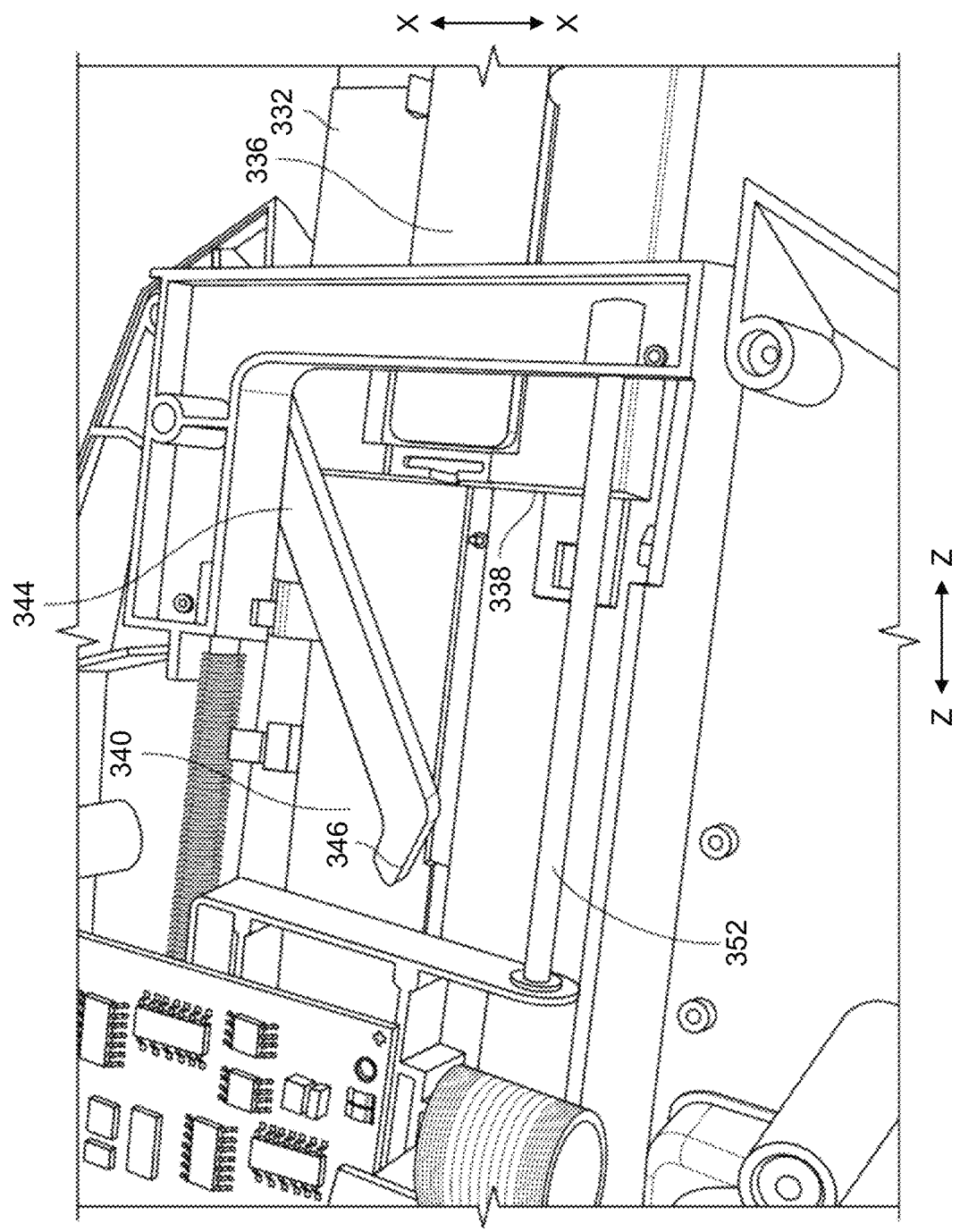
FIGS. 7A-7B are close-up views of the drawer in the apparatus in an open position (FIG. 7A) and in a closed position (FIG. 7B), with a test device positioned in the drawer.

FIG. 7A is an illustration of the internal components in the area of the drawer in the apparatus, which are visible to a user only upon removal of the housing. In FIG. 7A, drawer 332 is in its open position, and a test device 336 is positioned in the drawer for insertion into the apparatus. A distal edge 338 of drawer 332 remains inserted within the apparatus when the drawer is in its open position, with a proximal edge of the drawer being the portion of the drawer closest to a user and that enters and exists the apparatus during use. Within the apparatus is a receptacle 340 into which drawer 332 can be received when the drawer is moved into its closed position. Extending into receptacle 340 is a positioning arm 342 with a first end 344 and a second free end 346. First end 344 is movable within a track or slot 348 in the receptacle. The arm is dimensioned and positioned such that its free end 346, or at least a corner of the free end, of the arm contacts an edge of the test device 336 when the drawer is moving between its open and closed positions. This is apparent from the view shown in FIG. 7B, where the drawer is in its closed position and a corner of the free end of the arm is in contact with the test device, and specifically with an edge of housing surrounding a lateral flow immunoassay strip. The arm via its contact with the test device gently presses the test device to a specific position within the drawer, and more specifically within the slot in the drawer that is dimensioned to receive and hold the test device.

Arm 342 is dimensioned and positioned to ensure precise lateral positioning of the test device in the apparatus, more specifically, precise positioning in a plane that passes through the apparatus in a side to side direction with respect to the left/right sides of the apparatus. This plane is denoted by the x-x arrows in FIG. 7A. A second arm can also be provided, to precisely position the test device along an axis running from the front to back of the apparatus, referred to as a longitudinal axis and denoted by the z-z arrows in FIG. 7A. In one embodiment, a second arm is located at a proximal end 350 of the drawer, to press against the test device to position it in the horizontal plane. The second arm, in one embodiment, is under tension by a spring, and in other embodiments is movable laterally and positioned to have a pressure point when in contact with a frontal edge of the test device.

Figure 7B:
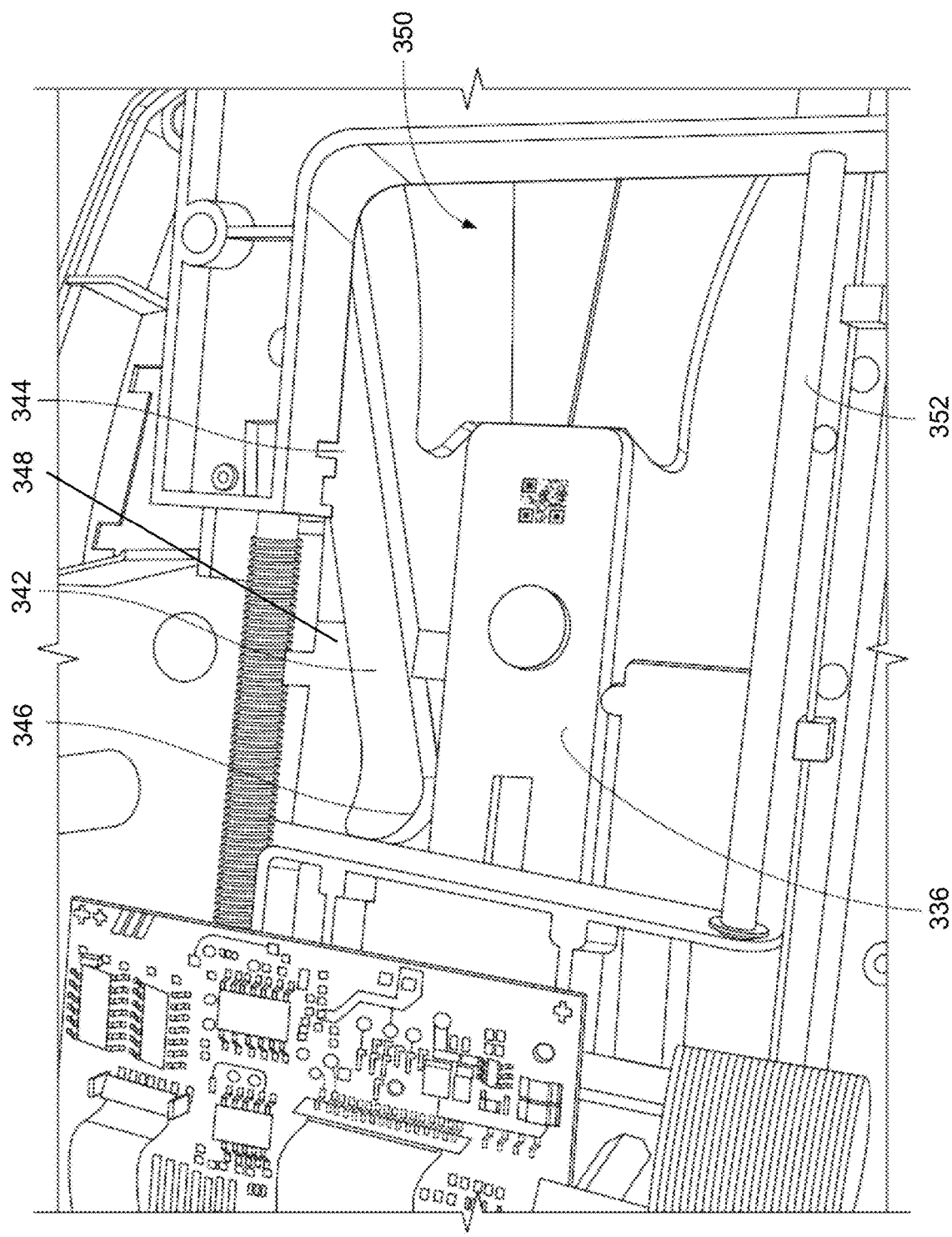
Figure 8:
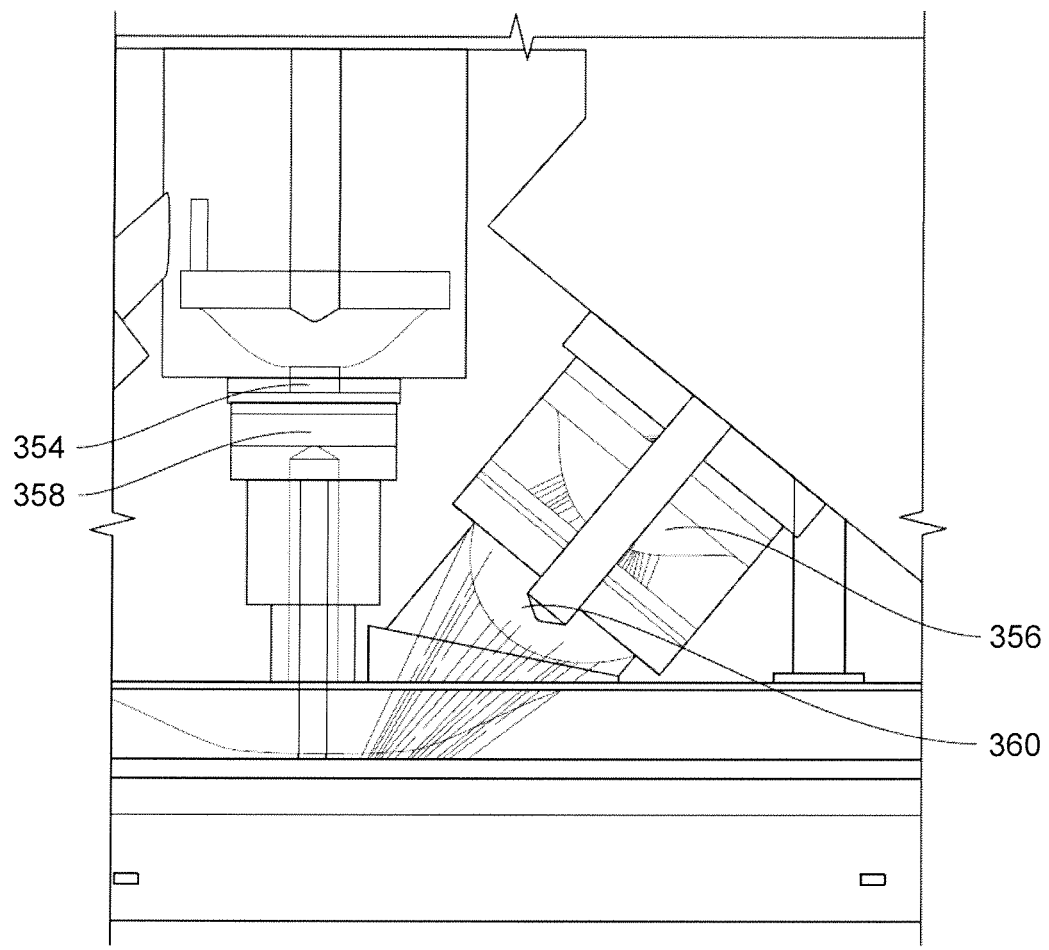
FIG. 8 is a schematic of the optics system within the apparatus.
Figure 9:
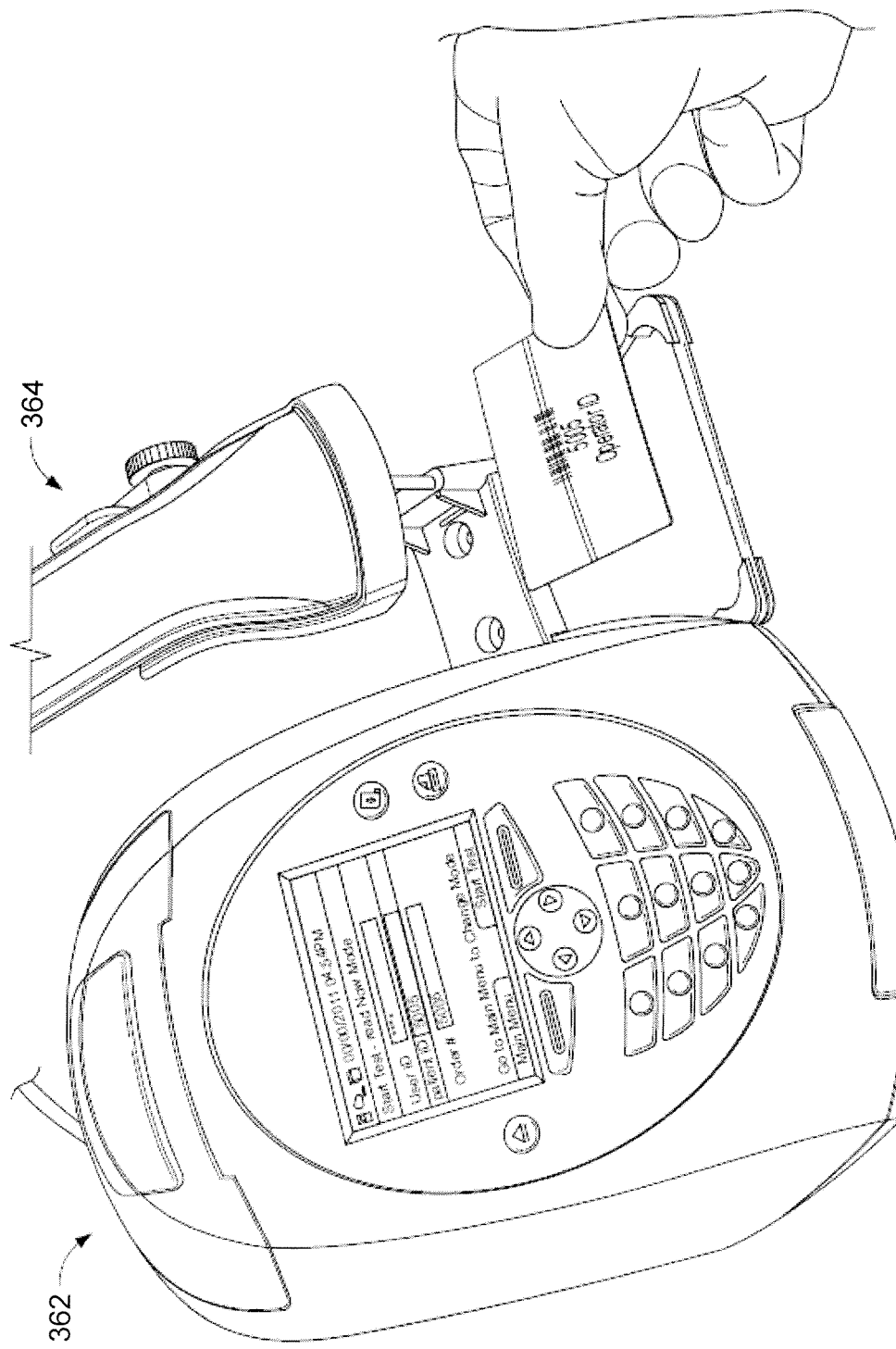
FIG. 9 is a view of an exemplary apparatus with an optional bar code scanner device attached.

Visible in FIGS. 7A-7B is a support rod 352 that extends at least the length of receptacle 340. Support rod 352 provides a track along which a movable optics system in the apparatus travels, to scan the stationary test device inserted into the apparatus. The optics system is now described with reference to FIG. 8.

A microprocessor-controlled optics system is positioned within the housing of the apparatus such that it moves along the longitudinal axis (denoted by the z-z arrows in FIG. 7A) from a home or start position to a final position. The optics system includes an optics module comprised of a carriage mounted on a track, the carriage movable by an electric motor or actuator within the optics system of the apparatus. Secured to the carriage, and part of the movable optics module, are an illumination source 354 and a detector 356, such as a photodiode. The illumination source can be mounted perpendicular to the test device and the detector is oriented at an angle to collect emission from the test device. In the embodiment shown in FIG. 8, a photodiode is oriented at 40° relative to the test device, and more generally the detector can be oriented at an angle of between about 20°-75° relative to the surface of the test device. In one embodiment, the optics module includes a single element optical detector (that is, an array of optical detectors is not present) and a single illumination source. The optics module can also comprise one or more filters, and the embodiment illustrated includes a filter 358, and preferably a long pass filter, on the emission side of the illumination source, and a filter 360 positioned between the test device and the detector. In one embodiment, the illumination source emits UV light at a wavelength that matches the excitation wavelength of a label in the test device. In one embodiment, the illumination source is a light emitting diode (LED) that has a peak emission at 365 nm, more generally of between about 320-390 nm or 325-380 nm. In this embodiment, the long pass filter positioned in the optical path from the LED to the test device transmits light between 310-315 nm.

In one embodiment, the photodetector is a broad band detector suitable to detect light at the wavelength emitted from the label in the test device. In one embodiment, the photodetector is a single-element photodetector (i.e., is not an array of photodetectors). In one embodiment, the label is or contains a fluorescent, luminescent, or chemiluminescent compound. As will be described below, an exemplary fluorescent label is a lanthanide ion, such as europium, samarium, terbium and holmium, which each fluoresce at specific wavelengths. Filter 360 positioned in the optical path between the test device and the detector, in one embodiment, transmits light above about 515 nm for detection by the detector. A skilled artisan will appreciate that a variety of filters are known in the art (longpass, shortpass, bandpass, etc.) and can be selected according to the wavelengths of light desired to excite a label and the wavelength of light desired for detection.

The optical system can also include an optical feedback loop. The intensity or light output of the illumination source is controlled by a feedback loop using a monitor diode in the illumination path of the optics. Power to the illumination source is adjusted based on light output, where if, for example, light output decreases, current is increased to compensate. In one embodiment, the power output from the illumination source is between 2-5 mW, more preferably between 2.5-5 mW. The feedback loop subsystem ensures consistent light output from the illumination source and reduces the frequency that calibration of the optical system in the apparatus is required.

Resolution of the optics system to resolve or discriminate individual, discrete lines on the test strip is a feature of the optics system, as will become apparent from the description of the test device and operation of the apparatus below. The illumination source preferably provides a focused beam of light capable of resolving one or more lines on an assay test strip that are between 1-1.2 mm apart, or 4 mm apart measured from the center of a first line and the center of an adjacent line. In one embodiment, the shape of the beam of light from the illumination source is 2.5 mm by 0.8 mm, more generally is between 2-3 mm by 0.5-1.2 mm. In another embodiment, the illumination source illuminates localized regions of the detection zone on a test device (described below) and the single-element detector is synchronized with the illumination source in incremental movement along a movement path, thus permitting synchronized illumination in a localized region and detection in the localized region. A field stop is provided to determine the shape of the beam of light, and can be tailored according to the spacing between and width of the test lines on the test strip. As will be described below, in one embodiment, the spacing or tolerance between two adjacent test lines on the test strip and the shape of the beam of light are selected to provide a dark space between test lines where no emissivity signal occurs.

In one embodiment, the optical system comprises a splash shield positioned between the sample input on the test device and the optical system, to protect the optics system and its movable module from liquid sample that may linger in the sample port/sample pad, particularly when the device is operated in walk-away mode, described below.

The apparatus, in some embodiments, includes a temperature sensing means, and in a preferred embodiment, includes at least two temperature sensing devices housed within the housing of the apparatus. A first internal temperature sensor is positioned to detect the temperature in the region associated with the optics system and a second internal temperature sensor is positioned elsewhere in the apparatus away from any internally generated heat source in order to detect ambient temperature of the environment in which the apparatus is operated.

The apparatus includes internal memory storage with necessary software for operation and for storage of data collected from sample analysis. By the SIM port or by an external computer (wireless or wired attachment), data can be exported from the apparatus or imported to the apparatus.

As mentioned above with reference to FIG. 5B, the apparatus is equipped with ports for attachment to optional external devices, and an example is illustrated in FIG. 5. In this embodiment, the front or user side of an apparatus 362 is shown, and attached to the apparatus is an external bar code scanner 364. The bar code scanner interfaces with the apparatus via a suitable data port provided on the apparatus. Externally attached devices ease transfer of data into and from the apparatus, and can eliminate user keyboard input, permitting accurate data input into the apparatus regarding a test to be analyzed or patient or sample information. In one embodiment, a barcode scanner external is attachable via PS-2 port on the apparatus and is capable of reading a linear or 1D bar code.

In one embodiment, the apparatus is wireless or wired connected to a device for delivering medical data to a third party, such as the Centers for Disease Control (CDC). In an exemplary embodiment, the apparatus communicates wirelessly with the 2Net™ Platform available from Qualcomm Life. The 2Net™ Platform is a cloud-based system that allows for the secure transfer of data from the apparatus for storage. The 2Net™ Platform gateways include, but are not limited to, a 2Net™ Hub, a stand-alone FDA-listed external device, and a cellular component embedded in the apparatus. Data from the apparatus is transferred to a cloud via a 2Net™ Platform gateway where it can be stored, manipulated, and/or shared. In an exemplary embodiment, the data may be transferred to the CDC for reporting and/or surveillance of infectious agents. In this embodiment, it is preferable that the date be manipulated, such as "de-identified", after transmission to the cloud storage to comply with applicable rules and regulations such as HIPAA. It will be appreciated that the data may be transferred to one or more cloud storage sites (e.g. from a third-party cloud such as Qualcomm to a proprietary cloud). In one specific non-limiting embodiment, data from the apparatus is wirelessly transmitted to a Qualcomm cloud via the 2Net™ Hub. the data is then transferred to a proprietary cloud where it is "de-identified" to remove user information for compliance with HIPAA rules and regulations. The data is then transferred to the CDC for surveillance of infectious agents.

The apparatus can include additional optional features, including for example acoustical output capability, to generate tones for audible feedback to a user, such as an error or test completion.

III. Calibration Cassette for Optics System

As described above, the apparatus comprises an optics system comprised of an optics module that includes a light source, which in one embodiment is an LED light source with a peak emission at 365 nm. The detector for the emitted signal, such as fluorescent light from a label in a test strip, is a photodiode with filters to ensure that the light from the fluorescent reagent is not contaminated by ambient nor excitation light. Signal from the photodiode is translated through an analog to a digital converter where the digital signal is processed by a microprocessor in the apparatus into a test result. To ensure consistent light output, the LED has a feedback loop whereby the optics system monitors the light output of the LED and triggers an adjustment of the electrical current to the LED to ensure a consistent intensity of the excitation light beam in real time. To further ensure that signal drift is controlled, the apparatus has a calibration algorithm that enables the user to insert a calibration cassette specifically designed for the apparatus and provided with the apparatus. The calibration cassette is illustrated in FIG. 10.

Figure 10:
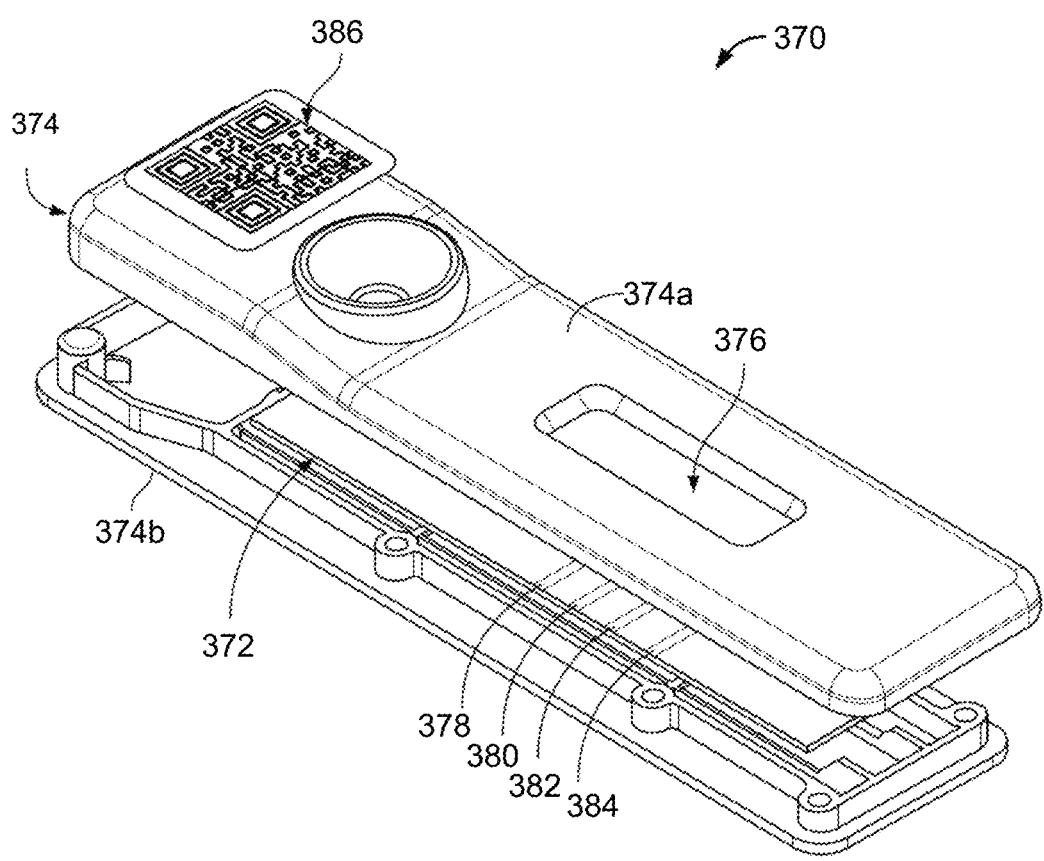
FIG. 10 is a view of a calibration cassette.

FIG. 10 shows a calibration cassette 370 comprised of a calibration strip 372 secured within a housing member, such as housing member 374 which is separable in this embodiment into upper member 374a and lower member 374b. A window 376 in upper housing member 374a is provided so that the optics system in the apparatus can interact with one or more lines on the calibration strip.

The calibration strip can comprise one or more lines, and in various embodiments, comprises two or more lines, three or more lines or four or more lines. In another embodiment, the calibration strip comprises at least two lines, at least three lines, or at least four lines. The embodiment illustrated in FIG. 10 shows a calibration strip with four lines, identified as 378, 380, 382 and 384, and referred to herein below as calibration lines or calibration test lines. The calibration lines are positioned on the strip relative to the housing to be visible through the window when the strip is secured within the housing. In one embodiment, the calibration strip is comprised of a material that fluoresces upon excitation by light from the illumination source in the optics system of the apparatus at a wavelength detectable by the photodiode subsequent to passage through any filter(s) in the light path of the photodiode. In one embodiment, the calibration strip is comprised of a material that fluoresces, and the calibration lines are defined by masking. For example, the fluorescing material can be silk-screened with a material that blocks light leaving the one or more calibration lines exposed. Alternatively, a fluorescing material can be deposited in discrete lines onto a non-fluorescing material. In one embodiment, the fluorescing material in the calibration strip is a fluorescent whitening agent deposited on or dispersed in a support material. Exemplary fluorescent whitening agents optical brightener are dyes that absorb light in generally the ultraviolet and violet range (340-370 nm) of the electromagnetic spectrum and re-emit light in the blue region (typically 420-470 nm). Exemplary optical brighteners include compounds such as stilbenes (di-, tetra, or hexa-sulfonated), coumarins, imidazolines, diazoles, triazoles, benzoxazolines, biphenyl-stilbenes. A specific exemplary class of compounds are thiophenediyl benzoxazole compounds, and a specific exemplary fluorescent whitening agent is 2,5-thiophenediylbis(5-tert-butyl-1,3-benzoxazole), an optical brightener. Exemplary support materials include polymers, and particularly plastics, such as polymethylmethacrylates and polyesters, in particular biaxially oriented polyester. The whitening agent can be polymerized with the support material during manufacture of the polymeric support material, or can be deposited onto the polymeric support after its manufacture. In a preferred embodiment, the fluorescing material forming the one or more calibration lines on the calibration cassette fluoresces between 500-550 nm when excited.

The calibration cassette can optionally include a label, such as bar code 386 on the cassette in FIG. 10. In one embodiment, the bar code is a two-dimensional bar code with information, for example, to confirm for the apparatus that the cassette is a calibration cassette and with information regarding an expiration date for the cassette.

The calibration cassette is dimensioned to fit within the drawer of the apparatus, for interaction with the optics system, and in one embodiment the apparatus and a dedicated, specific calibration cassette are provided together as a kit. A user of the apparatus, typically when prompted by the apparatus at a regular, defined period, such as every 30 days, or once a month, or once every two months, etc., inserts the calibration cassette into the drawer of the apparatus. The internal bar code reader within the apparatus transfers the information on the barcode of the calibration cassette to the processor in the analyzer. It will be appreciated that the internal bar code reader is an optional feature, as the information on the bar code label can be entered into the apparatus by a user using the key pad or via an external bar code scanner. From this information, the analyzer will confirm that a calibration cassette has been inserted into the analyzer, provide target signals the analyzer uses for comparison to actual signals obtained for the calibration lines on the calibration strip, and provide the expiration date of the calibration cassette. The analyzer then activates the optics system to initiate illumination of the calibration cassette, and specifically sequential illumination of each of the calibration lines visible within the calibration cassette window. The analyzer then detects the fluorescent signal from each of the calibration lines and stores the signal in memory. The detected signal for two of the calibration lines is compared to the target (expected) signal for that calibration line. If the detected signal for each of two of the calibration lines is within a predefined range of the target signal, for example within (+/-) 1.75, 2%, 2.25%, 2.5% or 3%, then the calibration of the analyzer is valid and no adjustments to the apparatus are needed. This calibration check event is recorded and stored in the memory of the apparatus.

If the detected signal for either or both of two of the calibration lines is outside the predefined range of the target signal, but not outside of a maximum predefined range, for example outside +/-3.25%, +/-3.5%, +/-3.75% or +/-4% of a predefined target signal for a specific line, the processer in the analyzer activates an algorithm to self-calibrate using a third or different calibration line on the calibration test strip. Information for the target (expected) signal from this third line is also in the barcode information and was conveyed to the apparatus upon insertion of the calibration cassette and scanning of the bar code. When the signal for this third calibration line is within a defined acceptable range, the analyzer again reads the first two calibration lines to confirm that the expected target signal is detected for these two lines. If the signal is outside the maximum range, the analyzer cannot recalibrate itself, and the system generates an error message that is displayed to the user.

Apparatus Software

The apparatus includes an integrated software system used to collect data from the lateral flow test assay, process the data, and display a result to the user. The software can vary according to, for example, the design of the lateral flow test assay. An exemplary test assay is described below along with software tailored to control the apparatus' interaction with the exemplary test assay. Here, a general description of the software requirements is provided.

The software requirements are based on the test strip features and requirements. These include the functional and non-functional requirements the software desirably meets in order to fulfill assay requirements and user needs. The software specifications preferably include three modes of user operation: Operator, Supervisor, and Service. In addition to the main user modes, the software specifications preferably include ethernet/Laboratory Information System (LIS) communication, printing, SD card interface and barcode scanner functionality. The software specifications preferably also provide power on/off processing, battery, error handling, languages and audio notification. The software specifications preferably comprise the following high level functions: analyzing fluorescent data from an assay test strip, a calibration cassette, or a quality control test; self calibration; managing users for login; storing, managing, and recalling test results; managing internal settings; printing results; sending results to a LIS; installing and operating in languages other than English; internal software checks, either at startup or continuously. In one embodiment, the software specifications preferably check all or some of the following, either at startup or continuously: memory, power supply; optics performance; stepper motor functionality; internal temperature; internal clocks; and barcode reading. If errors occur, they are logged in a message log and if applicable, the user is informed. The apparatus is designed to recover from errors in a safe manner.

Figure 11:
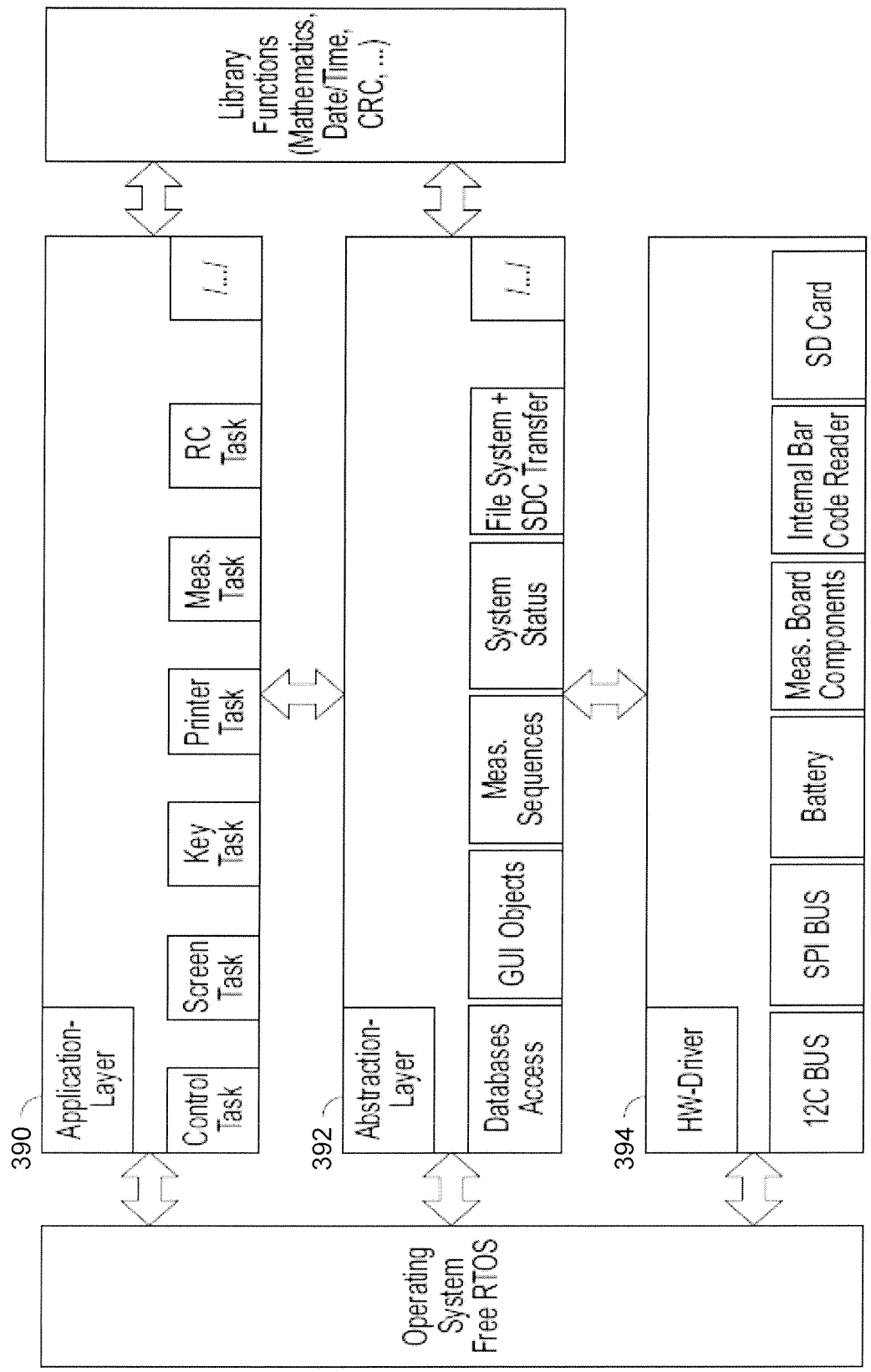
FIG. 11 is an illustration of the software architecture of an apparatus.

The apparatus software is based on 3-tier architecture, illustrated in FIG. 11. In brief, the software includes an application layer 390 that functions to controls the system tasks. These are separate tasks that run in parallel and perform dedicated functions. This includes, for example, controlling measurement scans, updating the graphical user interface (GUI) screens, accepting keypad user input, printing and performing remote communications. The tasks interact via message queues. A scheduler looks for tasks ready to run and activates them. The software also includes an abstraction layer 392 comprised of module groups that build up separate software subsystems. This builds a "convenience layer" for the application layer. The software subsystems include the data base subsystem, GUI objects, measured sequences, system status and SDC transfer. The software also includes a hardware (HW)-driver level 394 comprised of modules for communication with hardware components of the system over an application programming interface (API). The hardware components are the inter IC Bus (also known as the I2C-Bus, this component facilitates communication between electronic components), serial interface bus (SPI Bus), batteries, electronics, optional internal barcode reader and SD card.

As will be described further below, the software enables the apparatus to be operated in several modes, including a 'read now' mode where a test device inserted into the apparatus is immediately read; a 'walk away' mode where a test device inserted into the apparatus is incubated for a selected or predetermined period of time prior to being read; a mode to recall test results; a mode to recall control results. Accordingly, in one embodiment, the apparatus is designed to be operated in two or more, three or more or four or more modes.

III. Test Procedure and System Operation

As mentioned above, the apparatus can be operated in two modes, a 'read-now' mode or a 'walk-away' mode. The flow of sample from deposition on the sample pad to the absorbent pad takes between 2-20 minutes, more typically between 5-18 minutes, more typically between 7-15 minutes. A user can opt to place the sample on the sample pad of the test device, insert the test device into the drawer of the apparatus, and set the apparatus in 'walk-away mode' whereupon the apparatus will scan the bar code on the test device and determine the correct incubation time for the test device that permits sufficient time for the sample to flow from the sample pad to the absorbent pad. Alternatively, a user can opt to place the sample on the sample pad of the test device and incubate the test device external the apparatus. The test device is then inserted into the drawer of the apparatus subsequent to an incubation period external to the apparatus, and a user can operate the apparatus in 'read-now' mode wherein the apparatus will scan the bar code on the test device to determine the assay type and immediately initiate the scanning protocol for that assay type. In either mode, the test device and the apparatus are designed for interaction such that an accurate result is obtained irrespective of the incubation time. For example, a user may place the sample on the test device intending to utilize the apparatus in 'walk-away' mode, and encounter a distraction that causes the sample to incubate on the test device for a period of time prior to being inserted into the apparatus. In this situation, the incubation time of the sample on the test device will be longer than desired or required, introducing the possibility of a false positive result. By way of another example, a user may place the sample on the test device intending to carefully time the incubation time and to insert the test device after proper incubation into the apparatus, yet make an error in judging the incubation time. If the error results in over-incubation—i.e., a longer incubation time than desired or required for a particular analyte and test strip, a false negative may result. The test device and apparatus described herein are designed for interaction to render the test result insensitive to incubation time over an incubation period of about 1-15 minutes, preferably 2-10 minutes. This timing mechanism of the system and the scanning protocol and the processing of information from a scan will now be described, with reference to FIGS. 12-14, and the data in FIGS. 15-17 set forth in Example 1.

A. Operation of Apparatus

Figure 12:
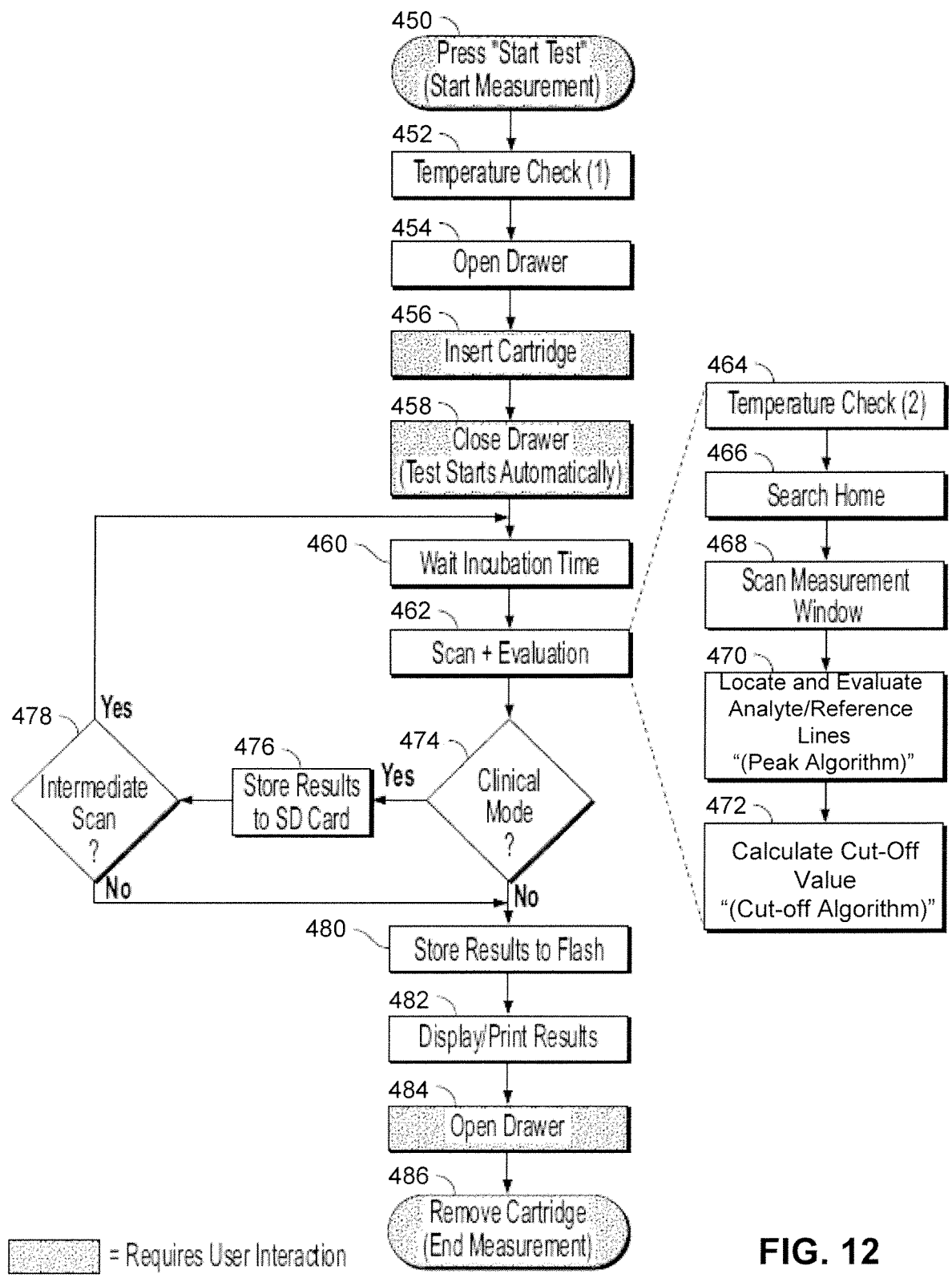
FIG. 12 shows the sequence of events in one embodiment of a measurement procedure where an apparatus as described herein interacts with a test device, exemplified by an immunoassay.

To initiate a scan of a test device, the apparatus is powered-on if needed and the toggle switch to initiate the apparatus software is activated. Prior to inserting the test device with sample into the apparatus, using the optional external bar code reader information about the user, the sample, the patient, etc. can be scanned into the apparatus memory. With reference to FIG. 12, a "start test" button on the apparatus or on the touch screen is pressed, 450, to start a measurement of a test device. The apparatus takes a temperature reading, 452, and then automatically opens the drawer in the apparatus, 454, to receive the test device on which a sample has been dispensed onto the sample pad. The test device with loaded sample is inserted into the drawer, 456, and the drawer is closed manually, 458, with gentle pressure by the user. As the drawer closes, one or more positioning arms press against the test device to position it in the drawer in a precise location that is consistent from test to test. The optics shield within the apparatus is positioned to protect the optics system and its movable optics module from any liquid sample that may splash from the sample input port when the drawer closes.

Closure of the drawer initiates a sequence of events, 458, comprised of the following. The internal bar code reader scans the bar code on the test device and receives information regarding the assay type (e.g., influenza NB, hCG, Strep A, RSV, etc.), the serial number and the expiration date of the test device, and any other information included on the bar code secured to the test device. In one embodiment, a mirror is positioned to facilitate interaction of the light beam from the internal bar code scanner and the bar code label on the test device. It will be appreciated that the internal bar code reader is an optional feature, as the information on the bar code label can be entered into the apparatus by a user using the key pad or via an external bar code scanner. Based on the test assay type discerned from the information on the bar code label or otherwise provided to the apparatus processor, the apparatus initiates an algorithm stored in the apparatus' memory for the assay for which the test device is designed, and based on user defined selection of read-now mode or walk-away mode, a protocol stored in memory initiates. In walk-away mode the apparatus incubates for a period of time, 460, prior to initiating a scan of the test device, 462; in read-now mode the apparatus does not wait for the preset incubation time for that particular assay, and immediately begins a scan of the test device, 462.

The scan and evaluation of the test device, 462, comprises another temperature check, 464, at the same or different position from the first temperature check 452. The initiated algorithm activates the optics system, including the stepper motor that moves the optics module with respect to the test device that is stationary in the apparatus. The optics system searches for its home position, 466, (described below) and then conducts a scan of the measurement window, 468, in the housing of the test device through which the reference/control and test line(s) are visible. The motor in the optics system moves the optics module incrementally from a defined start point along the length of the measurement window in the test device in accord with parameters defined by the algorithm for the particular assay being conducted. As will be described in more detail below, the optics module is moved in incremental steps by the motor in the optics system along the length of the test window, in a downstream to upstream direction with respect to sample fluid flow on the test strip, wherein the optics carriage stops at each incremental step or position to illuminate the position, detect emitted light after illumination at that position, before advancing upstream to the next position.

After collection of emitted light at each of the plurality of incremental positions along the length of the test window, the algorithm locates and evaluates the data in the data array that is associated with the reference line, 470, and conducts a qualitative, semi-quantative or quantitative analyte evaluation using a cut-off algorithm, 472.

The algorithm then determines whether the test is a clinical test, an external control or a calibration test, 474, and if the determination is yes (based on information provided on the test device bar code or based on user input information), the results are stored to memory, 476, such as on the SD card or in the apparatus memory. If the test is not a clinical test, then results are stored to flash memory, 480, and displayed and/or printed, 482. The drawer is then opened, 484, by the apparatus or by the user at the end of the measurement sequence for the user to remove the test device, 486.

Figures 13A, 13B:
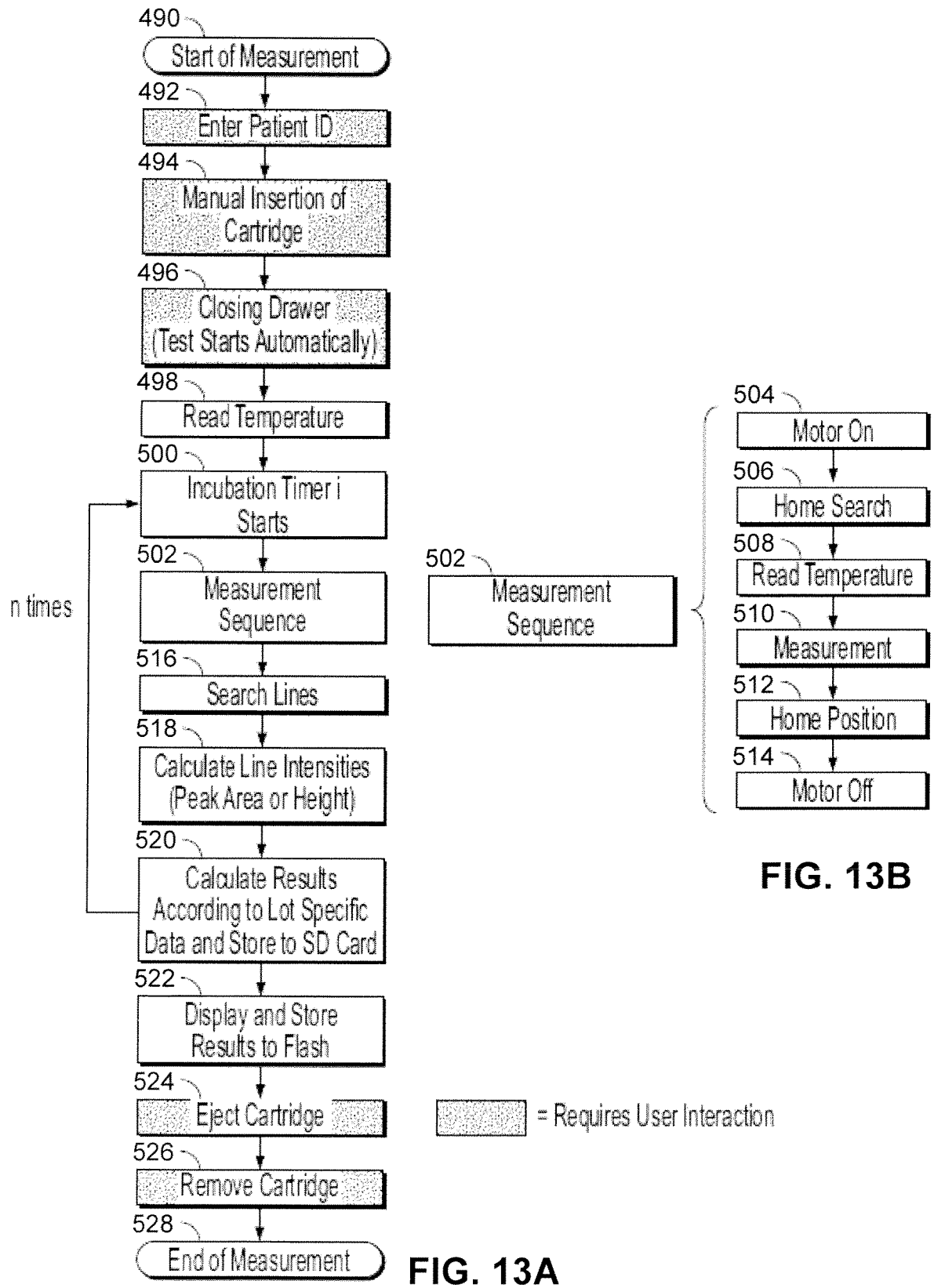
FIGS. 13A-13B show the sequence of events in another embodiment of a measurement procedure where an apparatus as described herein interacts with a test device, exemplified by an immunoassay.

FIGS. 13A-13B show a second exemplary test sequence for the apparatus described herein. It will be appreciated that the test sequence is easily varied by simply varying the programming in the software programs in the device, to alter the sequence of events, time allocated to each event, etc., in a measurement procedure. In the exemplary procedure of FIGS. 13A-13B, start of the measurement procedure is initiated, 490, by pressing a button or switch on the apparatus. Information regarding the patient (name, gender, age, etc.) is entered, 492, by the user via entry using the keypad on the apparatus or via an external bar code scanner. The drawer in the apparatus is opened using a button on the apparatus and the test device is inserted into the drawer, 494. Closing of the drawer manually or automatically by the apparatus initiates an automated sequence of events, 496. The sequence includes reading the temperature at one or more locations inside the apparatus, such as adjacent the test window, and/or taking an ambient temperature reading, 498. If an incubation time is commanded by a user selecting 'walk-away' mode or by a pre-programmed requirement for a particular test assay, an incubation time starts, 500. Upon completion of the incubation time or if no incubation time is required or commanded, the measurement sequence by the optics system automatically initiates, 502.

With reference now to FIG. 13B, the measurement sequence by the optics system includes activating the motor that moves the optics module, 504, and the optics module finding its home position, 506. A temperature reading, 508, in the vicinity of the optics system can be taken. At a first position along the optical read path that corresponds with the test window on the test device inserted in the apparatus, the illumination source in the optics module is turned on and then off, and during the off period fluorescent emission is detected by the photodetector in the optics module. The detected emission is stored in memory, and the motor in the optics system advances the optics module a fixed amount to its next position, which in an embodiment is in a direct toward the sample zone in the device so that measurement of the lines in the test window occurs in a downstream to upstream direction with respect to fluid flow on the test strip. After completion of a predefined number of incremental steps along the length of the test window and capture of light emission at each step, 510, the optics module is returned to its home position by the motor, 512, and the motor is powered off, 514. It will be appreciated from this description, that in one embodiment, the apparatus comprises a dynamic optics module of an illumination source and a photodetector, wherein the module is static during an illumination/detection sequence and resumes dynamic movement thereafter. It will also be appreciated that the dark reading, i.e, detected emission during the off, or dark period, of the illumination-detection sequence, is utilized for purposes of baseline and background and not for time-resolved fluorescence.

The algorithm stored in apparatus memory for that particular assay then searches the data array for the peak emissions for each of the test and reference lines, 516, to calculate line intensities of peak area or peak height, 518. The algorithm calculates results from the data array, 520, and stores the results to memory, such as on the SD card inserted into the device. The calculated result can be displayed to the screen on the apparatus, or prompted to be printed by the user, or stored in flash memory if needed, 522. A user can then instruct the apparatus to open the drawer, to remove the test device, 524, 526, ending the measurement procedure, 528.

In one embodiment, and with specific reference to a test device like that shown in FIG. 4 for detection and/or discrimination of two analytes in sample, such as influenza A and influenza B, the strip is incubated in the apparatus when operated in walk-away mode for approximately fifteen minutes, at which time the apparatus initiates an optical scan of the test device, measuring fluorescence signals across the strip's length and performs calculations and reports the test results. The scanning of the test device strip and analysis requires less than about 60 seconds, and more preferably is between about 20-60 seconds, more preferably 30-45 seconds.

The apparatus and the reference line on the test device are designed to interact in several ways to ensure that the correct result will be determined and reported. First, the location of the reference line on the test device is used by the algorithm in the apparatus to determine the relative locations of the analyte-specific test lines on the test device. The software program expects the reference line to be located within a specific, pre-defined location range. The acceptable range for the location of the reference line is based on the manufacturing tolerance for placement of immunochemistry on the test strip, for location of the test strip within the housing, and for positioning of the test device (test strip in the housing (cassette)) within the drawer of the apparatus. Once the reference line is located, the positions of each of the other test lines and zones are determined by the algorithm and match the locations of the various chemistries deposited on the test strip.

Figure 14A:
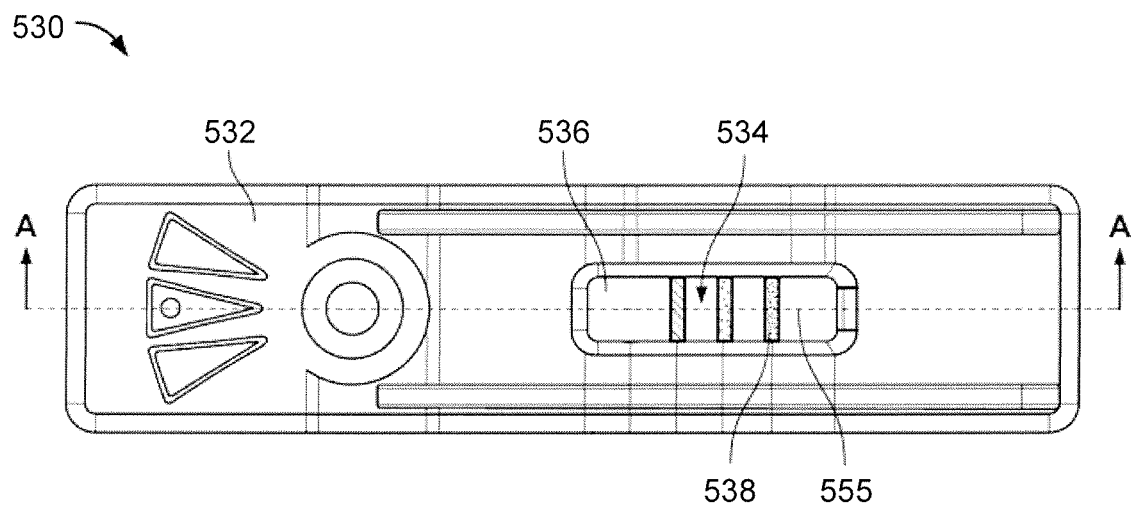
FIGS. 14A-14C correspond to a top view of a test device (FIG. 14A), a cross-sectional view of the test window region of the test device (FIG. 14B), and an exploded view of a portion of a test strip showing an embodiment of the arrangement of test lines, reference lines and control lines on a test strip (FIG. 13C)
Figure 14B:
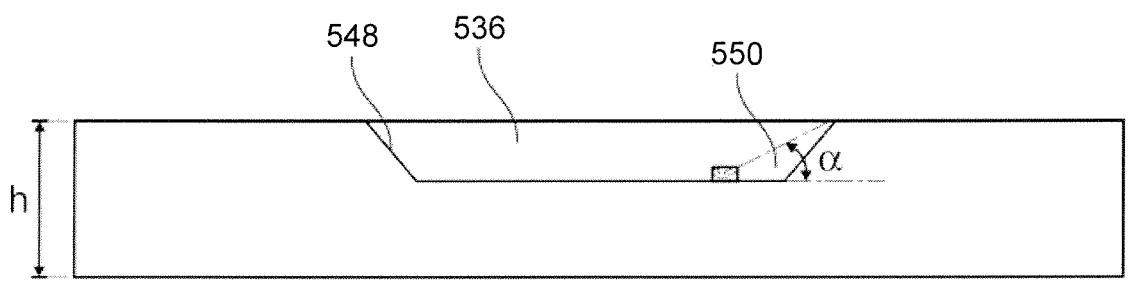
Figure 14C:
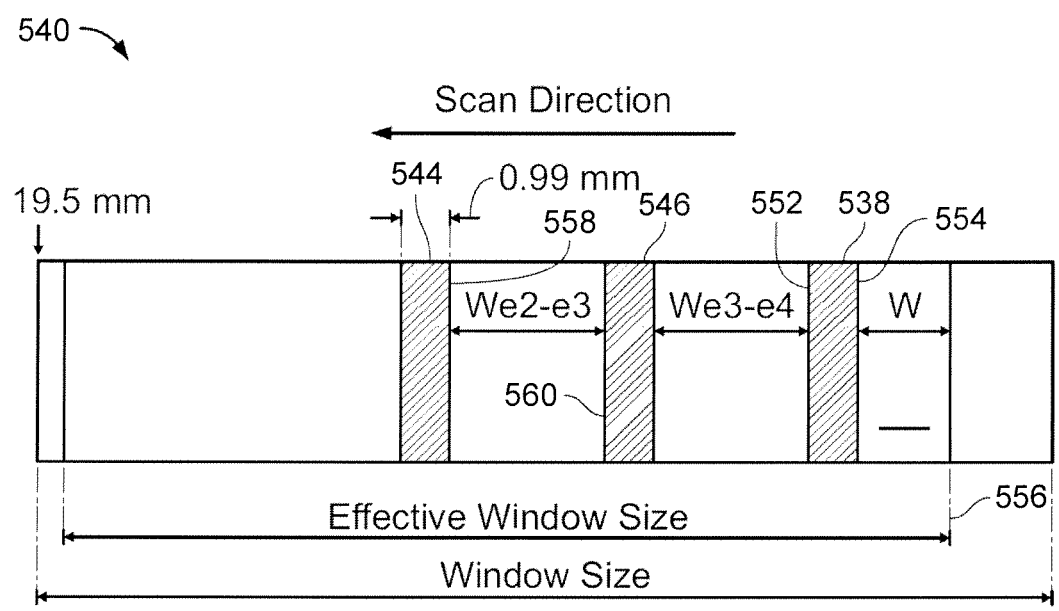

More specifically, and with reference to FIGS. 14A-14C, a top view of a test device 530 is shown, the test device having an external housing 532. Inserted inside the housing is a test strip 534, seen partially in FIG. 14A through the window 536 in the housing. The portion of test strip 534 comprising the reference line and at least one test line, also referred to herein as the "nitrocellulose region" of the test strip, is shown in FIG. 14C. A reference line 538 on the test strip is the distal most line on the test strip, relative to the proximal end of the test strip where the sample pad is positioned. That is, the reference line is the line furthest downstream (with respect to the direction of sample fluid flow) on the test strip. Because the optics system scans the nitrocellulose region visible through the test window in the housing in a downstream to upstream direction, as indicated by arrow 540 in FIG. 14C, where downstream to upstream is relative to sample fluid flow on the test strip, the reference line is the first line encountered with the optics system initiates its scan of the test device.

As mentioned above, the reference line is comprised of, for example, a binding member with specific binding affinity for either (i) an analyte in the sample that is not the analyte of interest (i.e., an analyte other than the analyte of interest) or (ii) a binding member for a reagent with specific binding affinity to an analyte in the sample that is other than the analyte of interest. In one embodiment, the reference line's relative fluorescence units (RFU) signal desirably exceeds a specified minimum (such as 500 RFUs, or 1,000 RFUs, or 1500 RFUs, or 2000 RFUs, etc.) in order to demonstrate adequate sample flow, otherwise the test is interpreted as invalid. The minimum RFU is information that may be provided on the bar code for each test device or is information stored in memory. It will be appreciated that the minimum RFU for a reference line in a test strip may be assay specific, where the minimum RFU for a test device for Strep A may be different than the minimum RFU for a test device that detects RSV. As mentioned above, the location of the reference line peak in the data array of RFU signals collected enables the use of an algorithm to locate the test line(s) on the test strip, thereby specifying the scanning location(s) for the test line(s). Alternatively, or stated differently, signal from the reference line permits the algorithm to identify the data in the array that corresponds to signal from the test line. That is, the reference line provides a signal between a maximum value and minimum value, and that signal is used to define the location of the reference line that may be used to identify areas to look for the other analyte lines. If there is no signal from the test lines then the analyte value is zero (i.e., the analyte is not present), and the test is negative. If there is a signal from a test line, that signal it will be identified as a valid signal if it comes from locations defined by the reference line position.

Figure 15:
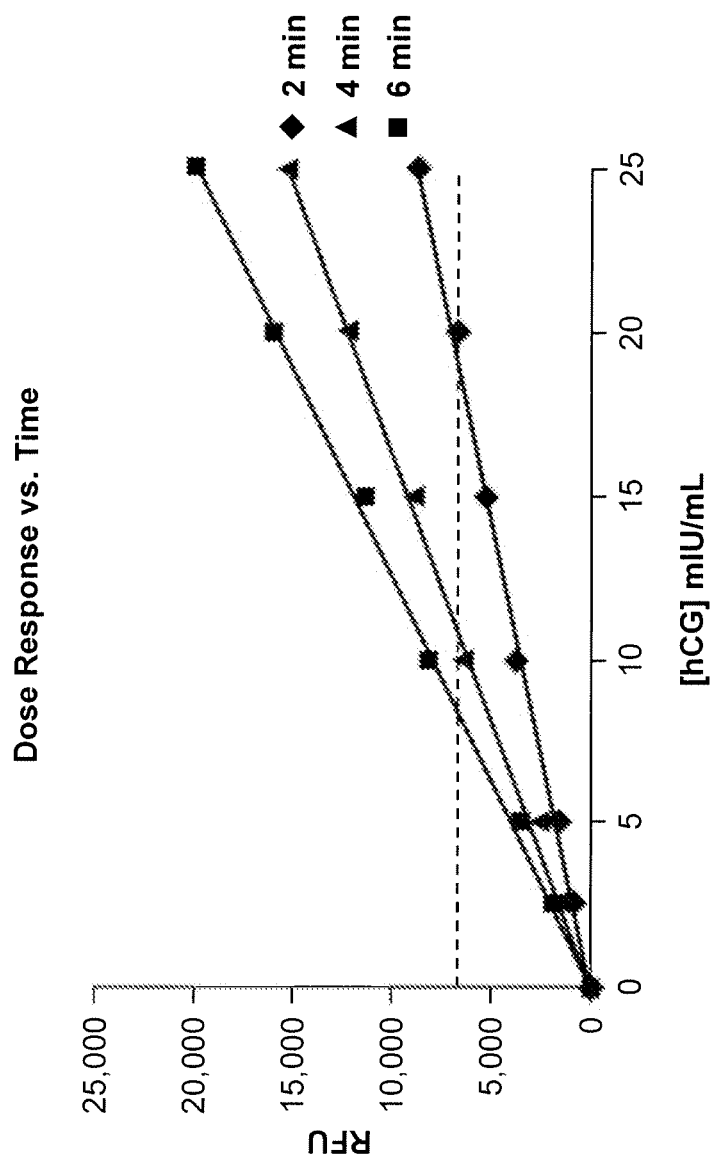
FIG. 15 is a graph of relative fluorescence units (RFU) from a test line on a test device for detection of hCG, where sample applied to the test strips contained hCG a concentration of 2.5, 5, 10, 15, 20 and 25 mIU/mL and the test strips were incubated for 2 minutes (diamonds), 4 minutes (triangles) or 6 minutes (squares)

The reference line also serves as a 'timer mechanism' for the system, i.e., the apparatus and test strip. This is achieved by programming the analyzer with an algorithm that uses the signal (e.g., RLU, RFU) from the reference line to determine a cut-off value unique to the individual test strip inserted into the apparatus, and against which signal from the test line(s) is compared to determine a test result. As a skilled artisan will appreciate, signal from a control, test or reference line on a test strip has a strong dependency on incubation time; i.e, the elapsed time from sample placement on the strip and visual inspection of the line to determine a test result. This dependency is illustrated in FIG. 15, where the relative fluorescence units (RFU) from a test line on an immunoassay test strip for detection of hCG at varying concentration, in mIU/mL, in a sample is shown. Samples with a concentration of 2.5, 5, 10, 15, 20 and 25 mIU/mL were placed on test strips, and the test strips were incubated for 2 minutes (diamonds), 4 minutes (triangles) or 6 minutes (squares). After the incubation time, RFU from the test line was read with the apparatus. The increase in RFU with increasing incubation time, at every concentration level, is apparent from the data. This data illustrates the problem with over incubation of a test strip and false positives. For example, an apparatus that is programmed with a fixed cut-off value of 7,000 RFU (indicated by the dashed line in FIG. 15), the cut-off value representing the minimum RFU value for a positive result, yields a valid result for a sample with a concentration of 10 mIU/mL only if the incubation time is at least 6 minutes. An apparatus programmed with a fixed cut-off value of 7,000 RFU would report a false negative for a sample with 10 mIU/mL incubated for less than 6 minutes.

The system of the present invention resolves this issue, by providing a reference line on the test strip that is used by the apparatus to determine an individual cut-off value for the test strip. In this approach, the signal (RFU, RLU) emitted from the reference line is detected by the apparatus and mathematically transformed to determine a cut-off value. This transformed cut-off value represents an individualized value for the particular test strip, and renders the test strip insensitive to incubation time. This is seen in the data presented in FIG. 16A. In this study, detailed in Example 1, urine samples with varying concentrations of hCG were placed on test strips and incubated for times from 2 minutes to 10 minutes. At the end of the incubation time, the signal from the reference line and test lines was detected. Signal from the reference line was mathematically transformed using exponentiation to determine a transformed cut-off value. In some embodiments, the exponentially transformed signal was further adjusted by a constant value that is empirically determined for each manufacturing lot of test strips. It will be appreciated that Example 1 is an exemplary embodiment where two populations of microparticle-antibody conjugates coated with uniquely different antibodies were prepared. A skilled artisan will appreciate that for some assays the same antibody for both spotting onto the test strip and attaching to the conjugate beads can be used.

Figure 16A:
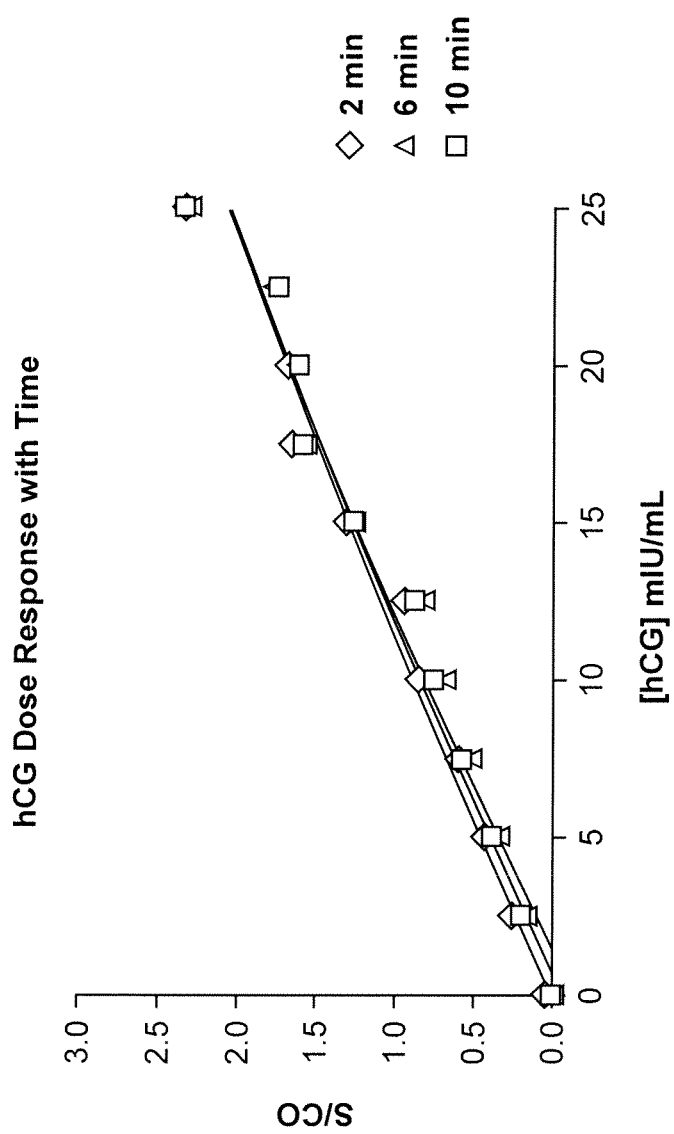
FIG. 16A is a graph of ratio of signal from test line to a transformed cut-off value for individual test strip, where a sample containing varying amounts of hCG is deposited on the test device and then incubated for incubation times of 2 minutes (diamonds), 6 minutes (squares) and 10 minutes (triangles) before reading signal from the test and reference lines.
Figure 16B:
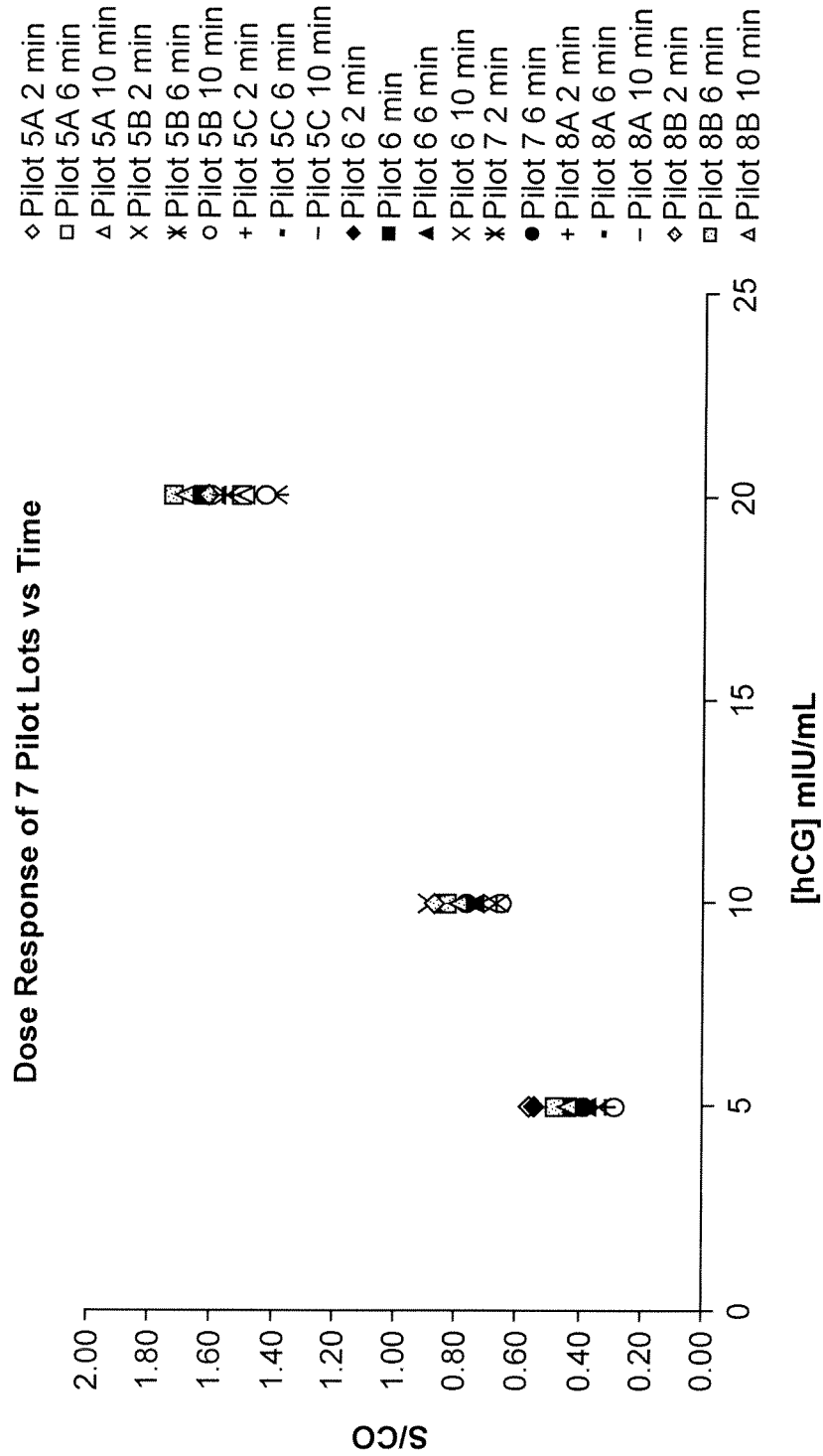
FIG. 16B is a graph of ration of signal from test line to a transformed cut-off value for individual test strips from seven manufacturing lots, where a sample containing varying amounts of hCG is deposited on each test strip which is then incubated for incubation times of 2 minutes (diamonds), 6 minutes (squares) and 10 minutes (triangles) before reading signal from the test and reference lines.

Signal detected from all or a portion of the population of particles captured at the test line was compared to the transformed cut-off value, and if the signal from the test line was above the transformed cut-off value the apparatus reported a positive test result. If the signal from the test line was below the transformed cut-off value the apparatus reported a negative result. FIG. 16A shows the data, where signal to transformed cut-off value for each individual test strip is shown as a function of concentration of hCG in the sample, for incubation times of 2 minutes (diamonds), 6 minutes (squares) and 10 minutes (triangles). The data shows that incubation time no longer a variable to the test result, as a test strip incubated for 2 minutes or 10 minutes provided the same ratio of signal to transformed cut-off value, and therefore a consistent test result irrespective of incubation time between 2-10 minutes. FIG. 16B presents data collected for test strips manufactures in seven different manufacturing lots to illustrate the consistency of the reference line in providing a mechanism to render the test strip insensitive to incubation time over a period of 1-15 minutes, or longer (e.g., 1-25 minutes).

A skilled artisan in view of the data in FIGS. 16A-16B will appreciate the advantages and novel approach of the reference line and mathematical transformation of the signal from the reference line to determine presence (or not) of an analyte of interest. The signal of the test line and the reference line are proportional to the length of time the assay has incubated, and by programming the analyzer with an algorithm to determine an individual cut-off value for the test strip, the dependency of signal on incubation time is removed. This approach solves the problems encountered when the incubation time is shorter or longer than needed for accuracy of a test result. For example, if the time between sample application and analyzer read of the test line is too long the resulting signal can be too high to yield an accurate result. A premature (under incubation) read time of a test line can result in a false negative as there has been an insufficient incubation time to generate a signal sufficient to be read by the analyzer as a positive. A test line read after a proscribed incubation time (over-incubated test strip) can result in a false positive because of the extra time permitted for accumulation of signal at the test line, and a signal that is close to but below a cutoff value preprogrammed into the analyzer. The reference line and algorithm in the analyzer described herein solve these problems.

The tolerance between lines (analyte-specific, reference and optional control) on the test strip is precise, so that the optics module illuminates directly above a middle region of the lines. The reference line in some embodiments is wider that the other lines on the test strip, to give the optics module a larger target for finding its point of reference. It will be appreciated that the lines require a certain minimum spacing to avoid overlap of peak emission so that a baseline can be determined between each line. With reference again to FIGS. 14B-14C, a cross-section of the window of a test device is shown, where the angle of the wall 548 of the test window 536 creates a shadow 550. The shadow decreases the actual window length to an effective window length. As seen in FIG. 14C, the reference line 538 has a certain width $w_{ref}$, that in one embodiment is larger than the width $w_{test}$, of an analyte-specific test line. The reference line has an upstream edge 552 and a downstream edge 554, with respect to the direction of fluid flow on the test strip. A procedural control zone 555 is defined by the downstream edge 554 of the reference line and the downstream end 556 of the effective window length. In one embodiment, the dimensional width of the procedural control zone 555 is less than the width between lines upstream of the reference line. For example, in the embodiment shown in FIG. 14C, test line 544 has a downstream edge 558 and test line 546 has an upstream edge 560. The distance between edges 558 and 560 defines a width, $w_{l1\_l2}$, between lines upstream of the reference line, and in one embodiment this width, $w_{l1\_l2}$, is greater than the width of the procedural control zone. The spacing $w_{l1\_l2}$, between two lines in the nitrocellulose region of the test strip, is determined in conjunction with the shape of the beam of light from the LED such that a dark space between two adjacent lines exists where no emissivity signal occurs. This ensures a baseline is detected between each peak emission from the sequential, adjacent test lines.

The optics system in the apparatus is an assembly of mechanical, electronic and optical components which serves to illuminate the test strip with an ultraviolet light-emitting diode (UV LED) and then collects, processes, and transforms the resulting signal (e.g, europium fluorescence) using a photodiode to an electronic signal that is converted by an analog-to-digital converter into useable analytical data. The LED is a semiconductor device which emits light (UV at 365 nm in one embodiment), and during a measurement procedure the LED is pulsed on and off at each incremental step of the optics system along the optical path defined by the test window. The resulting emission (fluorescence or reflectance) is collected by a photodiode during and between illumination pulses. The unprocessed signal is manipulated by subtracting the background signal (LED off) from the signal with the LED on. The optic system collects signal data expressed in RFUs from each of the lines (reference, test, and control), when the optics module is positioned at one of is plurality of incremental positions along the length of the nitrocellulose region on which the plurality of lines are disposed. In one embodiment, the dwell time of the optics module at each incremental step is on the order of 2000-8000 microseconds, more generally between 3000-4500 microseconds. It will be appreciated that the dwell time at each step can be varied to manipulate sensitivity of the assay, where a longer dwell time at each step will increase sensitivity, and dwell time can be decreased to decrease overall test time.

At the end of a scan of lines in the window, the data collected consists of emission signals from the test strip at the position when LED is on (365 nm) and emission signals from test strip at that position when LED is off. The difference between these values at each position is taken, and stored in memory as a one-dimensional array of the difference in emissivity at each position when LED is on and when LED is off. The data processing algorithm smoothes the data array using a local polynomial regression (of degree k) on the series of differential emissivity values equally spaced in the series (such as the Savitzky-Golay method), to determine a smoothed value for each point. In one embodiment, the algorithm smoothes 13 points in the array, and the first derivative of the smoothed data array is taken, and the peak/trough of the derivative peak height is determined to be the raw cut-off value. The raw cut-off value is transformed, preferably using a exponential transformation (e.g, raising the raw signal cut-off value by an exponent in the range of 1.2-1.9), to yield a transformed cut-off value unique to the test strip. A signal to transformed cut-off ratio corresponds to a simple ratio of the signal in RFUs obtained at a test line divided by its transformed cutoff. Signal data that is collected is processed using a Savitzky-Golay smoothing algorithm that uses a weighted average smoothing method that reduces unwanted electronic noise, while preserving actual test signals, including maxima, minima and peak width with little impact on their actual dimensions.

Figure 17A:
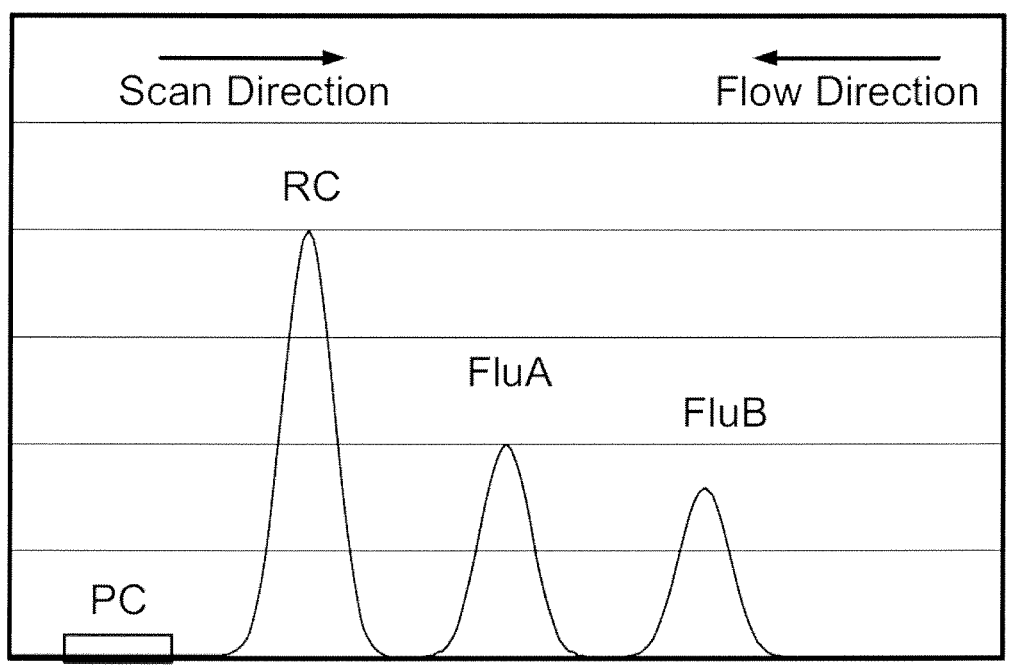
FIGS. 17A-17O are graphs showing an exemplary data set from an optical scan of a test device for detection of influenza A and influenza B, where the data is shown in arbitrary relative light units (RLU), as a function of position of the optics module (FIG. 17A), and the signal peak for the reference control line is presented as the first derivative to illustrate functioning of the algorithm to determine whether a peak is a maximum and not a minimum (FIG. 17B) and to determine peak height (FIG. 17C).
Figure 17B:
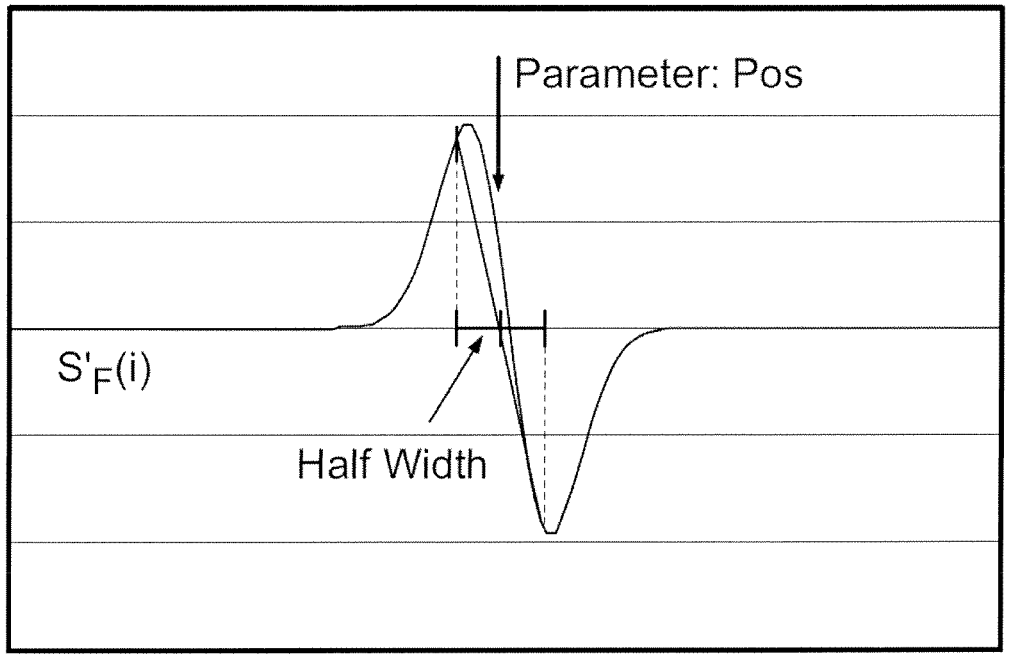
Figure 17C:
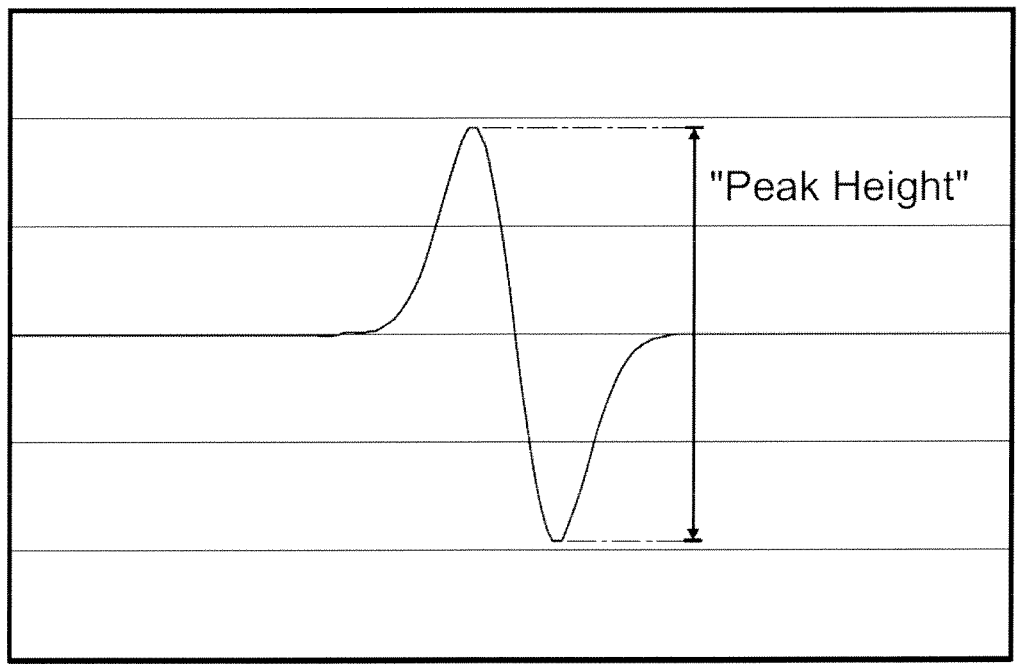

FIGS. 17A-17C are graphs showing an exemplary data set from an optical scan of a test device for detection of influenza A and influenza B. Upon completion of a scan of the test strip, a signal differential is determined for each incremental position by taking the difference between the signal detected during the illumination measurement where the LED is on (s(i)illum) and the signal detected during dark measurement where the LED is off (s(i)dark). This 'dark-corrected signal', s(i)DC, at each position i is calculated by:

$$sDC = sillum - sdark$$

The dark-corrected signal is checked for consistency by testing the condition:

$$sDC(i) > \text{MinDarkCorrCounts for all } i$$

where MinDarkCorrCounts corresponds to the minimal allowed value for the dark corrected signal. Conversion of signal index (i) to a position x in mm is done by:

$$x_{(i)} = x_{start} + \Delta x \cdot i$$

$$i_{(x)} = \text{roundtonearest}(x - x_{start})/\Delta x$$

where $x_{start}$ is the start position of the scan, x is the distance between two samples of the signal in mm.

Signal preparation is done by smoothing the signal and calculating the first derivative. Both the smoothed signal and the derivative of the smoothed signal are used as input parameters for a peak analysis. The first line in the scan, which corresponds to the reference line, is the position reference line for the other lines on the test strip. The reference line typically has a wider search range than the other lines, giving it a larger tolerance. Based on this positional control, the expected position (x) of the other peaks in the data set is known. The algorithm conducts a polarity check on the derivative of the peaks corresponding to the analyte-specific test line(s) and control line (if present), to determine if the peak is a maximum and not a minimum. As seen in FIG. 17B, the derivative of a positive peak (maximum) has a maximum, a zero crossing, and a minimum. The polarity check considers two points of the derivative; one is located half peak width (expected) left of the (expected) peak center; the other is half peak width right to center. If these points are connected by a straight line, this line must have a negative slope. A polarity check of the reference line is not typically done, as the positional tolerance for the reference line is high. The next step in peak detection is searching for a maximum and a minimum in the derivative, which is illustrated in FIG. 17B. Then, a peak height can be calculated, as shown in FIG. 17C. The algorithm calculates the peak height against a transformed cut-off value, and if the peak height is greater than the test strip individualized transformed cutoff value determined from the reference line on the test strip, the analyte is present and a positive result is reported.

The test strip can also include, in some embodiments, a negative control line as an optional feature. The negative control line is comprised of normal mouse immunoglobulin (IgG), and provides two functions. The negative control line enables measurement of the level of non-specific binding of the microparticle-antibody conjugates, thereby approximating the level of nonspecific binding that will occur on the test line(s). The negative control line also serves as an indicator of adequate incubation time and sample flow; e.g. if the RFU signal for the negative control line exceeds a specified maximum, adequate flow has not yet occurred and the assay is interpreted as invalid.

When a negative control line is present, a negative control threshold can be provided on the bar code information for each test device. The negative control threshold is a test strip lot-specific RFU (or RLU) value that impacts the calculation of the cut-off. For example, when the RFU of the negative control exceeds the negative control threshold value, then the cutoff calculation is changed from a fixed cutoff of 675 RFUs to a cutoff based on multiplying the RFU of the negative control value found on each test strip by a lot-specific correction factor. In another embodiment, a dual positive threshold value is provided for each test device, which corresponds to an RFU level used to determine the clinical outcome for a sample when the RFU signals for antigen A (e.g., influenza A) and for antigen B (e.g., influenza B) are both above their respective cutoffs—i.e. when a dual positive result is obtained. After the cutoffs for antigens A and B are determined, the RFU value of the antigens A and B test line signals are compared to this dual positive threshold value. Depending upon this comparison, a special algorithm may be triggered to calculate a positive or negative test result.

In summary, the apparatus and test device described herein include several features that are uniquely interactive to provide a sensitive, specific system. The test device includes, in one embodiment, a label pad with particles or micro-beads having a label or detectable moiety, such as a fluorescent material, and coated with antibodies with specific binding affinity for an analyte of interest. The test device includes a procedural control zone (PCZ) located after the last analyte-specific test line on the test strip. The procedural control zone is a region located between the last analyte test line and the absorbent pad. The analyzer scans this zone positioned at the downstream end of the test device, and determines whether adequate flow of the sample has occurred. A minimum and maximum fluorescent signal specification for this procedural control zone is one of the fail safe features incorporated into the assay. No colored test or procedural control lines will be visible to the human eye in the test window of the fluorescent assay cassette. The apparatus automatically scans the test strip, collects and analyzes the emitted signal (e.g., fluorescence data), and then calculates and reports the result. These features eliminate the subjectivity required to interpret results in visually human-read lateral flow assays. In addition, a negative control line located on the test strip, downstream of the label pad, and before an analyte specific test line. This negative control line serves as another procedural control and also as a source of information for calculating each assay's cutoff.

The assay's sensitivity is derived, in one embodiment, from the use of a unique polystyrene microbead that has been dyed with a chelate of europium. The europium compound (more than $1 \times 10^6$ fluorescent molecules per bead) that is encased within the microbeads is temperature stable, resistant to bleaching in room light, and yields a very efficient conversion of the UV energy from 365 nm to a wavelength of 618 nm. This large Stokes shift protects against many naturally occurring fluorescent compounds that may be present in the test materials and/or clinical specimens.

In view of the foregoing, a skilled artisan can appreciate that the concepts of using a procedural control zone and a timer mechanism are not limited to an apparatus that detects a fluorescent signal, but that fluorescent emission is merely exemplary of a detectable signal in general, and that an apparatus and test device that interact to provide and detect other signals are contemplated. For example, an apparatus that detects a reflectance signal is contemplated. Similarly, the test device need not be limited to a lateral flow immunoassay, as the concepts described herein are equally applicable to a test device designed to receive a sample and separate an analyte from the sample in a detectable way. Devices such as microfluidic devices and gels are examples.

B. Assays and Analytes to be Detected

The system comprised of an apparatus and a test device as described herein is intended for detection of any analyte of interest. Analytes associated with a disorder or a contamination are contemplated, including biological and environmental analytes. Analytes include, but are not limited to, proteins, haptens, immunoglobulins, enzymes, hormones, polynucleotides, steroids, lipoproteins, drugs, bacterial antigens, viral antigens. With regard to bacterial and viral antigens, more generally referred to in the art as infections antigens, analytes of interest include Streptococcus, Influenza A, Influenza B, respiratory syncytial virus (RSV), hepatitis A, B and/or C, pneumoccal, human metapneumovirus, and other infectious agents well known to those in the art.

In other embodiments, a test device intended for detection of one or more of antigen associated with Lyme disease, In another embodiment, a test device designed for interaction with the apparatus is intended for use in the field of women's health. For example, test devices for detection of one or more of fetal-fibronectin, chlamydia, human chorionic gonadotropin (hCG), hyperglycosylated chorionic gonadotropin, human papillomavirus (HPV), and the like, are contemplated.

The test devices are intended for receiving a wide variety of samples, including biological samples from human bodily fluids, including but not limited to nasal secretions, nasopharyngeal secretions, saliva, mucous, urine, vaginal secretions, fecal samples, blood, etc.

The test devices, in one embodiment, are provided with a positive control swab or sample. In another embodiment, a negative control swab or sample is provided. For assays requiring a external positive and/or negative control, the apparatus is programmed to request a user to insert into the apparatus a test device to which a positive control sample or a negative control sample has been deposited. Kits provided with the test device can also include any reagents, tubes, pipettes, swabs for use in conjunction with the test device.

IV. EXAMPLES

The following examples are illustrative in nature and are in no way intended to be limiting.

Example 1

Detection of a Human Chorionic Gonadotropin

A lateral flow test device comprised of a test strip and a housing was prepared. The test strip was fabricated to have a sample pad comprised of a glass fiber matrix in fluid connection with a nitrocellulose strip, one or both supported on a support membrane.

Using standard NHS/carboxyl chemistry, specific monoclonal antibodies were covalently bound to the surface of europium chelate (β-diketone)-incorporated polystyrene beads to form fluorescent microparticle-antibody conjugates. The microparticle-antibody conjugates were deposited on a glass fiber matrix to form a label pad. The label pad was positioned adjacent the sample pad in a downstream direction. Two populations of microparticle-antibody conjugates coated with uniquely different antibodies were prepared. One population of particles was comprised of particles coated with a monoclonal antibody for the beta subunit of hCG. A second population of detectable particles was comprised of detectable particles coated with a goat anti-rabbit IgG antibody specific for rabbit IgG. The first and second populations of particles were deposited in the label pad of the test strip.

A test line for capture of all or a portion of the first population of particles was prepared by depositing on the test strip a binding member with specific binding to the test analyte hCG at a location other than the binding between the antibody on the particles in the first population of particles. A reference line was prepared by depositing on the nitrocellulose, downstream from the test line, a binding member with specific binding to non-human or mouse IgG.

An absorbent pad comprised of a highly absorptive material that acts as a wick to draw fluid from the nitrocellulose strip, thereby helping to ensure that adequate sample flow through the entire test strip was achieved, was positioned on the test strip downstream from the label pad and the test and reference lines in the detection zone (also called nitrocellulose region).

The test strip was secured in a housing for ease of handling. On an external upper surface of the housing was a bar code label containing information about the test strip, including for example, the intended analyte to be detected (hCG), a device specific identification number, and an expiration date.

A urine sample spiked with a known amount of hCG was dispensed onto the sample pad via the sample input port in the housing. The test strip was inserted into the apparatus. The internal bar code scanner read the information on the bar code label on the test device to determine the assay type, the device lot number, the test device serial number and the test device expiration date. The microprocessor loaded the correct program into memory for the assay type to be run.

After a period of time programmed into the apparatus for waiting prior to reading a test strip for detection of hCG, the apparatus initiated its measurement sequence to scan the test device. The microprocessor-controlled optics unit in the apparatus conducted its incremental, step by step scan of the length of the viewing window, which approximately corresponds to the length of the detection zone/nitrocellulose region on the test strip. On the nitrocellulose strip the lines were sequentially read, beginning with the most downstream line, the reference line. The optics module moved relative to the stationary test device in an upstream direction to the analyte-specific test line. At each incremental step, UV light from the UV LED with a peak emission at 365 nm was flashed on and then off. The UV light excited the europium fluorophore which in turn emitted light at a wavelength of 618 nm.

After the apparatus completed its optical scan of the test window on the test device and collected the fluorescent data, it objectively interpreted the assay result. Signal emitted from the reference line was transformed by an exponential value of 1.4 to yield a transformed cut-off value. Signal from the test line was compared to the transformed cut-off value to determine presence of hCG in the sample. Results are shown in FIGS. 16A-16B.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A system, comprising:
   a test device comprising:
   (a) a label zone comprising
      (i) a first population of mobilizable, detectable particles for specific binding to a test analyte in a sample; and
      (ii) a second population of mobilizable, detectable particles for specific binding to a non-test analyte but not to the test analyte;
   (b) a first detection site at a first position comprising a first binding member having specific binding affinity for detectable particles in the first population bound to the test analyte; and
   (c) a second detection site at a second position that is separate from the first position, the second detection site comprising a second binding member having specific binding affinity for detectable particles in the second population bound to the non-test analyte; and
   an analyzer comprising:
   (1) a drawer dimensioned to receive the test device,
   (2) an optical system for detection of a signal generated from the first population of mobilizable, detectable particles at the first position and the second population of mobilizable, detectable particles at the second position when each population reaches a specific and separate position on the test device,
   (3) a motor to move a detector in the optical system from the first detection site to the second detection site,
   (4) a processor communicatively coupled with the optical system to receive the signal from the detector and to evaluate a ratio of a signal detected from all or a portion of the first population of mobilizable, detectable particles to a cut-off value to determine a presence or an absence of analyte in the sample based on the ratio, and
   (5) a memory storing the cut-off value, wherein the cut-off value is an exponentially transformed signal from all or a portion of the second population of mobilizable, detectable particles, adjusted by a constant value empirically determined for a manufacturing lot comprising the test device.

2. The system of claim 1, wherein the signal from all or a portion of the first population of mobilizable, detectable particles is used by the processor to provide a quantitative or semi-quantitative amount of analyte present in the sample.

3. The system of claim 1, wherein signal from the second population of mobilizable, detectable particles is mathematically transformed by the processor in the analyzer to provide a transformed signal.

4. The system of claim 3, wherein the signal from the second population of mobilizable, detectable particles is mathematically transformed by the processor using an exponential transformation.

5. The system of claim 4, wherein the exponential transformation is selected from an exponential value of between 1.3-1.8.

6. The system of claim 1, wherein the test device is a lateral flow immunoassay.

7. The system of claim 6, wherein one or both of the first population of mobilizable, detectable particles and the second population of mobilizable, detectable particles is comprised of particles comprised of a fluorescing lanthanide compound.

8. The system of claim 7, wherein the fluorescing lanthanide compound is europium.

* * * * *